US012578340B2

(12) United States Patent
    Eriksson et al.

(10) Patent No.: US 12,578,340 B2
(45) Date of Patent: Mar. 17, 2026

(54) DETERMINATION OF CANINE TK1 PROTEIN LEVELS

(71) Applicant: ALERTIX VETERINARY DIAGNOSTICS AB, Djurhamn (SE)

(72) Inventors: Staffan Eriksson, Lidingö (SE); Henrik Rönnberg, Uppsala (SE); Kiran Kumar Jagarlamudi, Uppsala (SE)

(73) Assignee: ALERTIX VETERINARY DIAGNOSTICS AB, Djurhamn (SE)

( * ) Notice: Subject to any disclaimer, the term of this patent is extended or adjusted under 35 U.S.C. 154(b) by 532 days.

(21) Appl. No.: 18/328,056

(22) Filed: Jun. 2, 2023

(65) Prior Publication Data

US 2024/0044903 A1     Feb. 8, 2024

Related U.S. Application Data

(60) Provisional application No. 63/348,653, filed on Jun. 3, 2022.

(51) Int. Cl.
    *G01N 33/574*    (2006.01)
    *C07K 16/40*     (2006.01)
    *C12Q 1/48*      (2006.01)
    *G01N 33/543*    (2006.01)
    *G01N 33/573*    (2006.01)
    *G01N 33/575*    (2026.01)

(52) U.S. Cl.
    CPC ....... *G01N 33/57585* (2026.01); *C07K 16/40* (2013.01); *G01N 33/54386* (2013.01); *G01N 33/573* (2013.01); *C12Q 1/485* (2013.01); *G01N 2333/9122* (2013.01)

(58) Field of Classification Search
    CPC .... C07K 16/40; C07K 16/18; C07K 2317/20; C07K 2317/34; G01N 33/541; G01N 33/5434; G01N 33/573; G01N 33/574; G01N 2800/52; G01N 2800/54
    See application file for complete search history.

(56) References Cited

U.S. PATENT DOCUMENTS

2010/0266495 A1    10/2010    O'Neill
2019/0185582 A1    6/2019    Eriksson et al.

FOREIGN PATENT DOCUMENTS

EP    1627230 B1    9/2010

OTHER PUBLICATIONS

Jagarlamudi, Kiran Kumar et al., A New Sandwich ELISA for Quantification of Thymidine Kinase 1 Protein Levels in Sera from Dogs with Different Malignancies can Aid in Disease Management, PLOS One, vol. 10, No. 9, pp. 1-15 (Sep. 14, 2015).

(Continued)

*Primary Examiner* — Vanessa L. Ford
*Assistant Examiner* — Rudolph E. Sloup, Jr.
(74) *Attorney, Agent, or Firm* — Porter Wright Morris & Arthur LLP

(57)    ABSTRACT

A kit useful for determination of canine TK1 in a sample is disclosed. The kit comprises a first monoclonal antibody, or a fragment thereof, immobilized to a support or intended to be immobilized to a support. The kit also comprises a second monoclonal antibody, or a fragment thereof. One of the monoclonal antibodies has specificity for a peptide consisting of an amino acid sequence from a C-terminal region of canine TK1 and the other monoclonal antibody has specificity for a peptide consisting of an amino acid sequence from an active site of TK1.

17 Claims, 11 Drawing Sheets

Specification includes a Sequence Listing.

(56)    References Cited

OTHER PUBLICATIONS

Jagarlamudi, Kiran Kumar et al., Properties of cellular and serum forms of thymidine kinase 1 (TK1) in dogs with acute lymphocytic leukemia (ALL) and canine mammary tumors (CMTs): Implications for TK1 as a proliferation biomarker, BMC Veterinary Research, vol. 10, No. 228, pp. 1-26 (2014).

Alegre, Melissa et al., Serum Detection of Thymidine Kinase 1 as a Means of Early Detection of Lung Cancer, Anticancer Research, vol. 34, pp. 2145-2152 (2014).

Carlsson, Lena et al., Elevated levels of thymidine kinase 1 peptide in serum from patients with breast cancer, Upsala Journal of Medical Sciences, vol. 114, pp. 116-120 (2009).

Jagarlamudi, Kiran Kumar, Immunoassays for detection of serum Thymidine kinase 1 in Dog lymphomas and carcinomas, Master Thesis in Animal Sciences, pp. 1-35 (2010).

Jagarlamudi, Kiran Kumar et al., High levels of inactive thymidine kinase 1 polypeptide detected in sera from dogs with solid tumours by immunoaffinity methods: Implications for in vitro diagnostics, The Veterinary Journal, pp. 1-8 (2013).

Hanan Sharif et al., Quaternary structures of recombinant, cellular, and serum forms of Thymidine Kinase 1 from dogs and humans, BMC Biochemistry, vol. 13, No. 12, pp. 1-10 (2012).

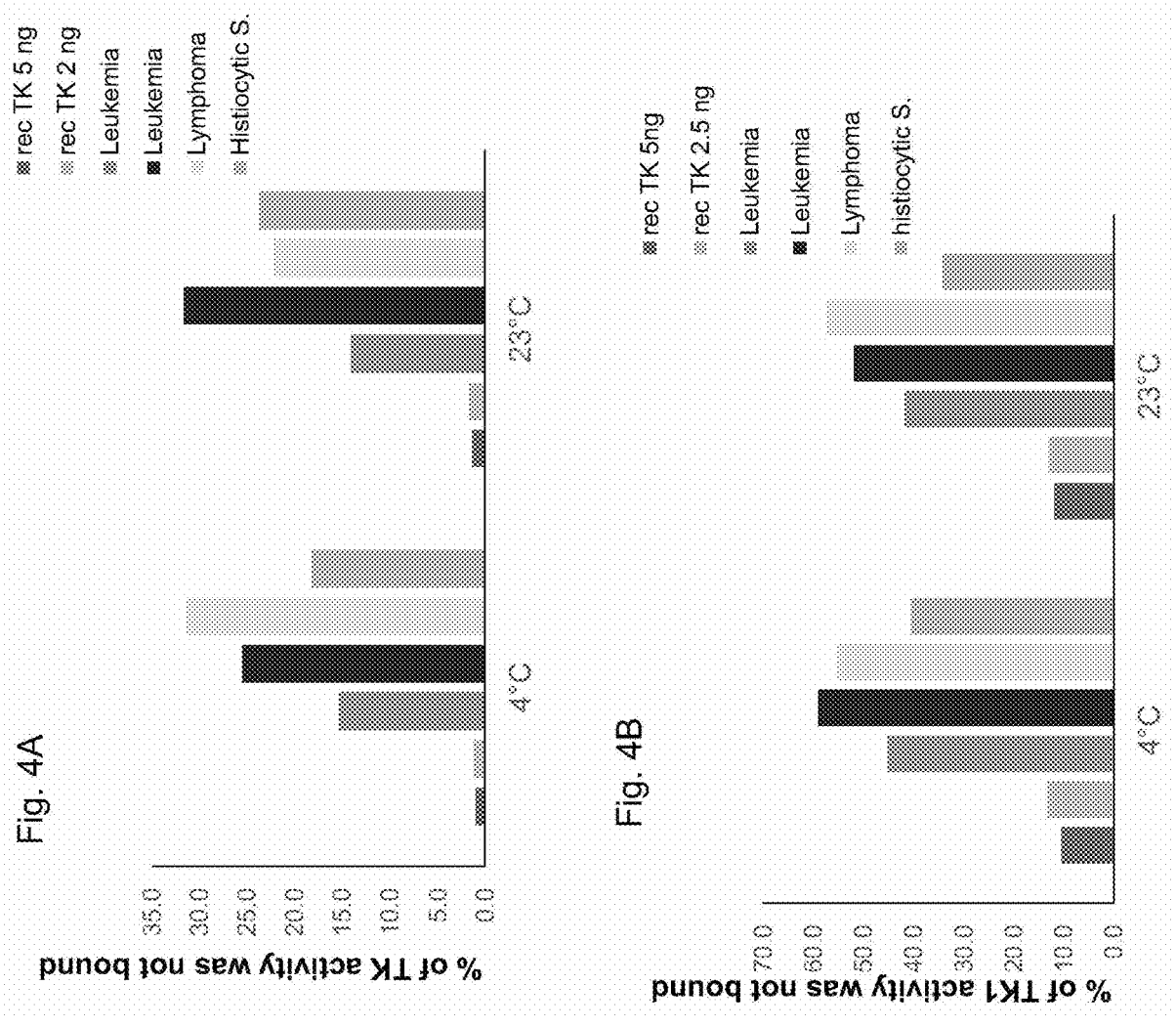

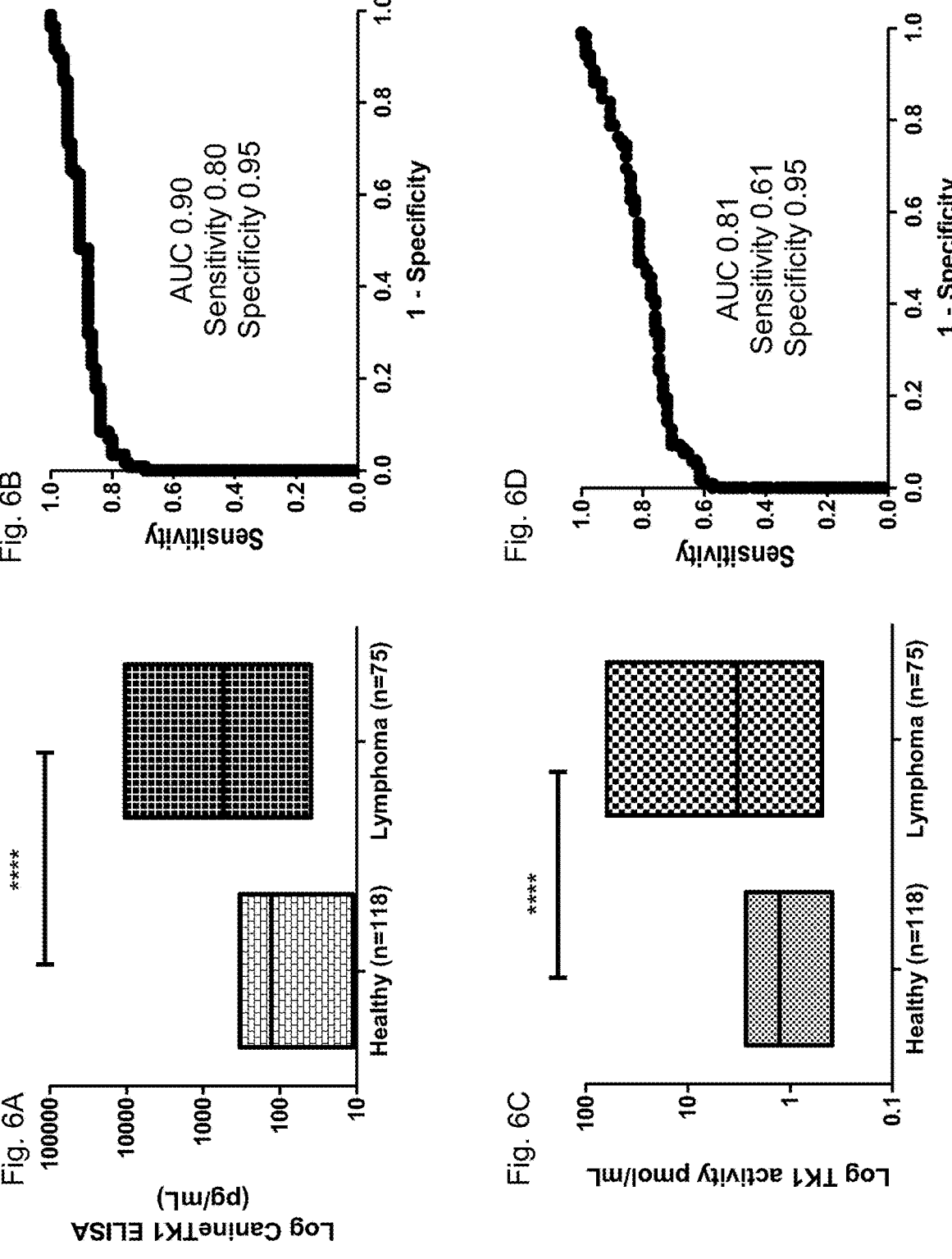

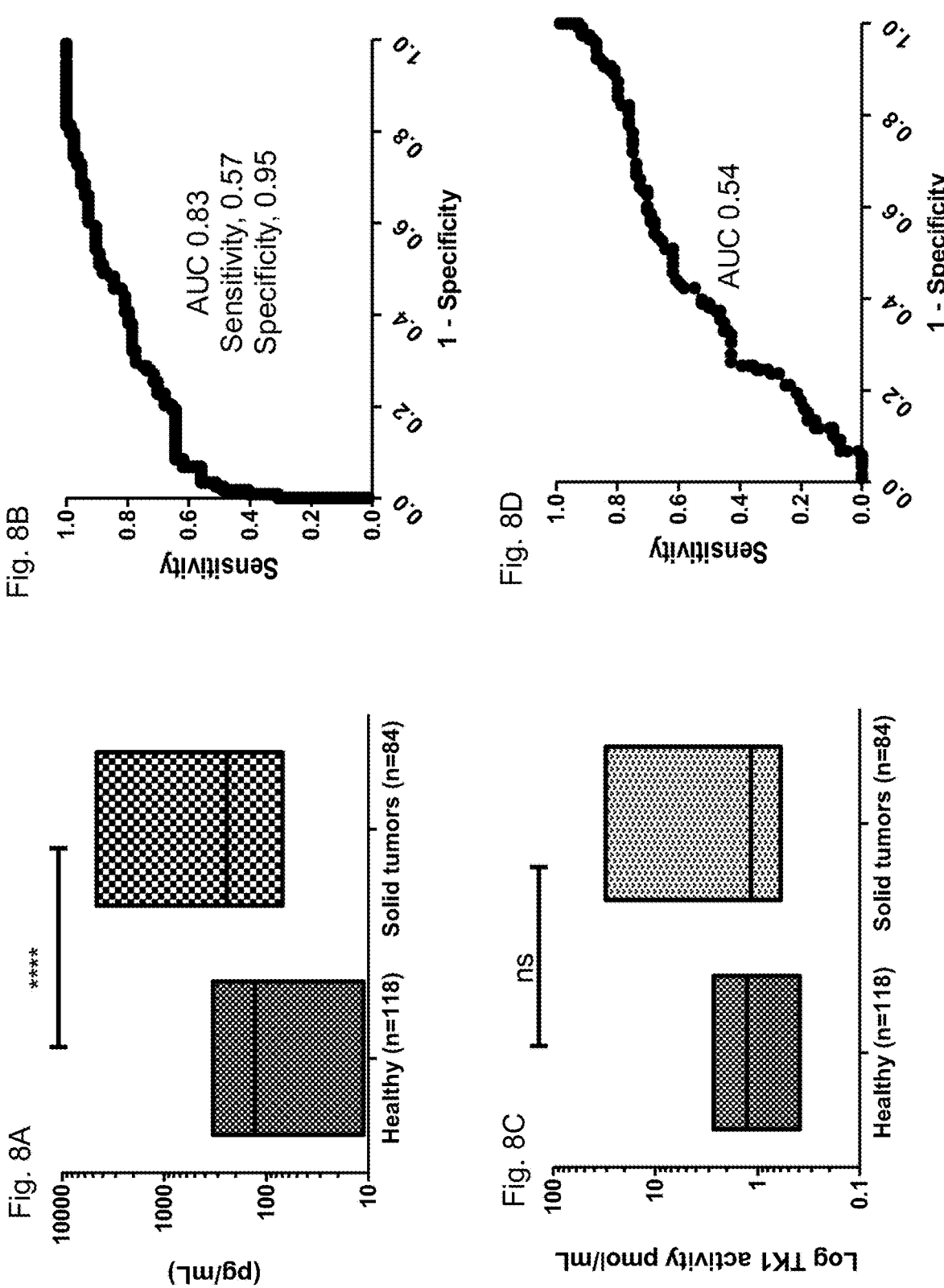

SEQUENCE LISTING

Sequence total quantity: 54
SEQ ID NO: 1             moltype = AA  length = 242
FEATURE                  Location/Qualifiers
source                   1..242
                         mol_type = protein
                         organism = Canis lupus
SEQUENCE: 1
MSCINLPTVL PGSPSKTRGQ IQVILGPMFS GKSTELMRRV RRFQIAQYKC LVIKYAKDTR    60
YSNSFSTHDR NTMEALPACL LRDVAQEALG VAVIGIDEGQ FFPDIVEFSE TMANAGKTVI   120
VAALDGTFQR KAFGTILNLV PLAESVVKLT AVCMECFREA AYTKRLGSEK EVEVIGGADK   180
YHSVCRLCYF KKASGPPMGL DSRENKENVL VLVPGKPGEG KEATGVRKLF APQHVLQCSP   240
AN                                                                 242

SEQ ID NO: 2             moltype = AA  length = 234
FEATURE                  Location/Qualifiers

```
source                      1..234
                            mol_type = protein
                            organism = Homo sapiens
SEQUENCE: 2
MSCINLPTVL PGSPSKTRGQ IQVILGPMFS GKSTELMRRV RRFQIAQYKC LVIKYAKDTR   60
YSSSFCTHDR NTMEALPACL LRDVAQEALG VAVIGIDEGQ FFPDIMEFCE AMANAGKTVI  120
VAALDGTFQR KPFGAILNLV PLAESVVKLT AVCMECFREA AYTKRLGTEK EVEVIGGADK  180
YHSVCRLCYF KKASGQPAGP DNKENCPVPG KPGEAVAARK LFAPQQILQC SPAN        234

SEQ ID NO: 3                moltype = AA   length = 237
FEATURE                     Location/Qualifiers
source                      1..237
                            mol_type = protein
                            organism = Felis catus
SEQUENCE: 3
MSCINLPTVL PGSPSKTRGQ IQVILGPMFS GKSTELMRRV RRFQIAQYKC LVIKYAKDTR   60
YSSSFSTHDR NTMEALPACL LRDVAQEALG VAVIGIDEGQ FFPDIVEYSE TMANAGKTVI  120
VAALDGTFQR KAFGTILNLV PLAESVVKLT AVCMECFREA AYTKRLGAEK EVEVIGGADK  180
YHSVCRLCYF KKASGLPAGP DGKENKENCP LLGKPGEASG ARKLFAPHQI LQCSSAN     237

SEQ ID NO: 4                moltype = AA   length = 237
FEATURE                     Location/Qualifiers
source                      1..237
                            mol_type = protein
                            organism = Equus caballus
SEQUENCE: 4
MSCINLPTVL PGSPSKTRGQ IQVILGPMFS GKSTELMRRV RRFQIAQYKC LVIKYAKDTR   60
YSSNFSTHDR NTMEALPACQ LRDAAQEALG VAVIGIDEGQ FFPDIVEFSE AMANAGKTVI  120
VAALDGTFQR KAFGAILNLV PLAESVVKLT AVCMECFREA AYTKRLGTEK EVEVIGGADK  180
YHSVCRLCYF KKPLGQPAGL DSTENKENFP VLGKPGEATG ARKLFAPHQI LQCSTAN     237

SEQ ID NO: 5                moltype = AA   length = 23
FEATURE                     Location/Qualifiers
source                      1..23
                            mol_type = protein
                            organism = Homo sapiens
SEQUENCE: 5
AYTKRLGTEK EVEVIGGADK YHS                                           23

SEQ ID NO: 6                moltype = AA   length = 24
FEATURE                     Location/Qualifiers
REGION                      1..24
                            note = Antigenic peptide
source                      1..24
                            mol_type = protein
                            organism = synthetic construct
SEQUENCE: 6
CAYTKRLGTE KEVEVIGGAD KYHS                                          24

SEQ ID NO: 7                moltype = AA   length = 23
FEATURE                     Location/Qualifiers
source                      1..23
                            mol_type = protein
                            organism = Canis lupus
SEQUENCE: 7
AYTKRLGSEK EVEVIGGADK YHS                                           23

SEQ ID NO: 8                moltype = AA   length = 24
FEATURE                     Location/Qualifiers
REGION                      1..24
                            note = Antigenic peptide
source                      1..24
                            mol_type = protein
                            organism = synthetic construct
SEQUENCE: 8
CAYTKRLGSE KEVEVIGGAD KYHS                                          24

SEQ ID NO: 9                moltype = AA   length = 15
FEATURE                     Location/Qualifiers
source                      1..15
                            mol_type = protein
                            organism = Canis lupus
SEQUENCE: 9
VLVPGKPGEG KEATG                                                    15

SEQ ID NO: 10               moltype = AA   length = 16
FEATURE                     Location/Qualifiers
REGION                      1..16
                            note = Antigenic peptide
```

```
source                  1..16
                        mol_type = protein
                        organism = synthetic construct
SEQUENCE: 10
CVLVPGKPGE GKEATG                                                              16

SEQ ID NO: 11           moltype = DNA   length = 1383
FEATURE                 Location/Qualifiers
misc_feature            1..1383
                        note = Heavy chain DNA sequence
source                  1..1383
                        mol_type = other DNA
                        organism = synthetic construct
SEQUENCE: 11
atgaagttgt ggctgaactg gattttcctt ggaacacttt taaatggtat ccagtgtgag    60
gtgaagctgg tggagtctgg aggaggcttg gtgcagcctg gggattctct gagactctcc   120
tgtgcaactt ctgggttcac cttcaatgat cactacatga actgggtccg ccagcctcca   180
ggaaaggcac ttgagtgggt ggcttttatt ggaaacaaag cttatggtta caaaataagaa   240
tacaattcat ctgtgaaggg tcggttcacc atctccagag atgactccca gagcttcctc   300
tatcttcaat tgaacaccct gagatctgag gacagtgcca cttattactg tgcaagagat   360
ggtgccttta tttattgggg ccaagggact gtggtcactg tctctgcagc caaaacgaca   420
cccccatctg tctatccact ggcccctgga tctgctgccc aaactaactc catggtgacc   480
ctgggatgcc tggtcaaggg ctatttccct gagccagtga cagtgacctg gaactctgga   540
tccctgtcca gcggtgtgca caccttccca gctgtcctgc agtctgacct ctacactctg   600
agcagctcag tgactgtccc ctccagcacc tggcccagcg agaccgtcac ctgcaacgtt   660
gcccaccggg ccagcagcac caaggtggac aagaaaattg tgcccaggga ttgtggttgt   720
aagccttgca tatgtacagt cccagaagta tcatctgtct tcatcttccc cccaaagccc   780
aaggatgtgc tcaccattac tctgactcct aaggtcacgt gtgttgtggt agacatcagc   840
aaggatgatc ccgaggtcca gttcagctgg tttgtagatg atgtggaggt gcacacagct   900
cagacgcaac cccgggagga gcagttcaac agcactttcc gctcagtcag tgaacttccc   960
atcatgcacc aggactggct caatggcaag gagttcaaat gcagggtcaa cagtgcagct   1020
ttccctgccc ccatcgagaa aaccatctcc aaaaccaaag gcagaccgaa ggctccacag   1080
gtgtacacca ttccacctcc caaggagcag atggccaagg ataaagtcag tctgacctgc   1140
atgataacag acttcttccc tgaagacatt actgtggagt ggcagtggaa tgggcagcca   1200
gcggagaact acaagaacac tcagcccatc atggacacgg atggctctta cttcgtctac   1260
agcaagctca atgtgcagaa gagcaactgg gaggcaggaa atactttcac ctgctctgtg   1320
ttacatgagg gcctgcacaa ccaccatact gagaagagcc tctcccactc tcctggtaaa   1380
tga                                                                  1383

SEQ ID NO: 12           moltype = AA   length = 460
FEATURE                 Location/Qualifiers
REGION                  1..460
                        note = Heavy chain
source                  1..460
                        mol_type = protein
                        organism = synthetic construct
SEQUENCE: 12
MKLWLNWIFL GTLLNGIQCE VKLVESGGGL VQPGDSLRLS CATSGFTFND HYMNWVRQPP     60
GKALEWVAFI GNKAYGYKIE YNSSVKGRFT ISRDDSQSFL YLQLNTLRSE DSATYYCARD    120
GAFIYWGQGT VVTVSAAKTT PPSVYPLAPG SAAQTNSMVT LGCLVKGYFP EPVTVTWNSG    180
SLSSGVHTFP AVLQSDLYTL SSSVTVPSST WPSETVTCNV AHPASSTKVD KKIVPRDCGC    240
KPCICTVPEV SSVFIFPPKP KDVLTITLTP KVTCVVVDIS KDDPEVQFSW FVDDVEVHTA    300
QTQPREEQFN STFRSVSELP IMHQDWLNGK EFKCRVNSAA FPAPIEKTIS KTKGRPKAPQ    360
VYTIPPPKEQ MAKDKVSLTC MITDFFPEDI TVEWQWNGQP AENYKNTQPI MDTDGSYFVY    420
SKLNVQKSNW EAGNTFTCSV LHEGLHNHHT EKSLSHSPGK                          460

SEQ ID NO: 13           moltype = DNA   length = 717
FEATURE                 Location/Qualifiers
misc_feature            1..717
                        note = Light chain DNA sequence
source                  1..717
                        mol_type = other DNA
                        organism = synthetic construct
SEQUENCE: 13
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgtacac agtaatggaa acacctattt acattggtac   180
ctgcagaagc caggccagtc tccaaagctc ctgatctaca agtttccaa ccgatttct     240
ggggtcccag acaggttcag tggcagtgga tcagggtcag atttcacact caagatcagc   300
agagtggagg ctgaggatct gggagtttat ttctgctctc aaagtacaca tattccgtac   360
acgttcggag gggggaccga gctggagata aagacgggctg atgctgcacc aactgtatcc  420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660
actcacaaga tcaacttcc cccattgtc aagagcttca caggaatga gtgttag        717

SEQ ID NO: 14           moltype = AA   length = 238
FEATURE                 Location/Qualifiers
```

-continued

```
REGION                   1..238
                         note = Light chain
source                   1..238
                         mol_type = protein
                         organism = synthetic construct
SEQUENCE: 14
MKLPVRLLVL MFWIPASSSD VVMTQTPLSL PVSLGDQASI SCRSSQSLVH SNGNTYLHWY    60
LQKPGQSPKL LIYKVSNRFS GVPDRFSGSG SGSDFTLKIS RVEAEDLGVY FCSQSTHIPY   120
TFGGGTELEI RRADAAPTVS IFPPSSEQLT SGGASVVCFL NNFYPKDINV KWKIDGSERQ   180
NGVLNSWTDQ DSKDSTYSMS STLTLTKDEY ERHNSYTCEA THKTSTSPIV KSFNRNEC     238

SEQ ID NO: 15            moltype = DNA   length = 1434
FEATURE                  Location/Qualifiers
misc_feature             1..1434
                         note = Heavy chain DNA sequence
source                   1..1434
                         mol_type = other DNA
                         organism = synthetic construct
SEQUENCE: 15
atgaaatgca gctgggttat cttcttcctg atggcagtgg taacaggggt caattcagag    60
gttcaactac agcagtctgg ggcagagctt gtgaagccag gggcctcagt caaattgtcc   120
tgcacagctt ctggcttcaa cattaaagac acctatatgc actgggtgaa acagaggcct   180
gaacagggcc tggagtggat tggaaggatt gatcctgcga atggtaatac taaatatgac   240
ccgaagttcc agggcaaggc cactataaca ccagacacat cctccaccac agcctacctg   300
cagctcagca gcctgacatc tgaggacact gccgtctatt actgtgctag aaatcgggcc   360
tactatggta actactatgc tatggactac tggggtcaag gaacctcagt caccgtctcc   420
tcagccaaaa caacacccc atcagtctat ccactggccc ctgggtgtgg agatacaact   480
ggttcctccg tgactctggg atgcctggtc aagggctact ccctgagtc agtgactgtg   540
acttggaact ctggatccct gtccagcagt gtgcacacct cccagctct cctgcagtct   600
ggactctaca ctatgagcag ctcagtgact gtccctcca gcacctggcc aagtcagacc   660
gtcacctgca gcgttgctca cccagccagc agcaccacgg tggacaaaaa acttgagccc   720
agcgggccca tttcaacaat caacccctgt cctccatgca aggagtgtca caatgcccca   780
gctcctaacc tcgagggtgg accatccgtc ttcatcttcc ctccaaatat caaggatgta   840
ctcatgatct ccctgacacc caaggtcacg tgtgtggtgg tggatgtgag cgaggatgac   900
ccagacgtcc agatcagctg gtttgtgaac aacgtgaag tacacacagc tcagacacaa   960
acccatagag aggattacaa cagtactatc cgggtggtca gcaccctccc catccagcac  1020
caggactgga tgagtggcaa ggagttcaaa tgcaaggtca acaacaaaga cctcccatca  1080
cccatcgaga gaaccatctc aaaaattaaa gggctagtca gagctccaca agtatacatc  1140
ttgccgccac cagcagagca gttgtccagg aaagatgtca gtctcacttg cctggtcgtg  1200
ggcttcaacc ctggagacat cagtgtggag tggaccagca tgggcatac agaggagaac  1260
tacaaggaca ccgcaccagt cctggactct gacggttctt acttcatata tagcaagctc  1320
aatatgaaaa caagcaagtg ggagaaaaca gattccttct catgcaacgt gagacacgag  1380
ggtctgaaaa attactacct gaagaagacc atctcccggg ctccgggtaa atga        1434

SEQ ID NO: 16            moltype = AA   length = 477
FEATURE                  Location/Qualifiers
REGION                   1..477
                         note = Heavy chain
source                   1..477
                         mol_type = protein
                         organism = synthetic construct
SEQUENCE: 16
MKCSWVIFFL MAVVTGVNSE VQLQQSGAEL VKPGASVKLS CTASGFNIKD TYMHWVKQRP    60
EQGLEWIGRI DPANGNTKYD PKFQGKATIT PDTSSTTAYL QLSSLTSEDT AVYYCARNRA   120
YYGNYYAMDY WGQGTSVTVS SAKTTPPSVY PLAPGCGDTT GSSVTLGCLV KGYFPESVTV   180
TWNSGSLSSS VHTFPALLQS GLYTMSSSVT VPSSTWPSQT VTCSVAHPAS STTVDKKLEP   240
SGPISTINPC PPCKECHKCP APNLEGGPSV FIFPPNIKDV LMISLTPKVT CVVVDVSEDD   300
PDVQISWFVN NVEVHTAQTQ THREDYNSTI RVVSTLPIQH QDWMSGKEFK CKVNNKDLPS   360
PIERTISKIK GLVRAPQVYI LPPPAEQLSR KDVSLTCLVV GFNPGDISVE WTSNGHTEEN   420
YKDTAPVLDS DGSYFIYSKL NMKTSKWEKT DSFSCNVRHE GLKNYYLKKT ISRSPGK      477

SEQ ID NO: 17            moltype = DNA   length = 723
FEATURE                  Location/Qualifiers
misc_feature             1..723
                         note = Light chain DNA sequence
source                   1..723
                         mol_type = other DNA
                         organism = synthetic construct
SEQUENCE: 17
atggaatcac agactcaggt cctcatgtcc ctgctgttct gggtatctgg tacctgtggg    60
gacattgtga tgacacagtc tccatcctcc ctgactgtga cagcaggaga gaaggtcact   120
atgagctgca agtccagtca gagtctatta aacagtcgaa tcaaaagaa ctacttgacc   180
tggtaccagc agaaaccagg gcagcctcct aaactgttga tctactgggc atccactagg   240
gaatctgggg tccctgatcg cttcacaggc agtggatttg gaacagattt cactctcgcc   300
atcagcagtg tgcaggctga agacctggca gtttattatt gtcaaaatga ttatagttat   360
ccattcacgt tcggctcggg gacaaagttg gaaataaaac gggctgatgc tgcaccaact   420
gtatccatct tcccaccatc cagtgagcag ttaacatctg gaggtgcctc agtcgtgtgc   480
ttcttgaaca acttctaccc caaagacatc aatgtcaagt ggaagattga tggcagtgaa   540
cgacaaaatg gcgtcctgaa cagttggact gatcaggaca gcaaagacag cacctacagc   600
```

-continued

```
atgagcagca ccctcacgtt gaccaaggac gagtatgaac gacataacag ctatacctgt   660
gaggccactc acaagacatc aacttcaccc attgtcaaga gcttcaacag gaatgagtgt   720
tag                                                                723

SEQ ID NO: 18            moltype = AA  length = 240
FEATURE                  Location/Qualifiers
REGION                   1..240
                         note = Light chain
source                   1..240
                         mol_type = protein
                         organism = synthetic construct
SEQUENCE: 18
MESQTQVLMS LLFWVSGTCG DIVMTQSPSS LTVTAGEKVT MSCKSSQSLL NSRNQKNYLT   60
WYQQKPGQPP KLLIYWASTR ESGVPDRFTG SGFGTDFTLA ISSVQAEDLA VYYCQNDYSY   120
PPTFGSGTKL EIKRADAAPT VSIFPPSSEQ LTSGGASVVC FLNNFYPKDI NVKWKIDGSE   180
RQNGVLNSWT DQDSKDSTYS MSSTLTLTKD EYERHNSYTC EATHKTSTSP IVKSFNRNEC   240

SEQ ID NO: 19            moltype = AA  length = 5
FEATURE                  Location/Qualifiers
REGION                   1..5
                         note = VH CDR1
source                   1..5
                         mol_type = protein
                         organism = synthetic construct
SEQUENCE: 19
DHYMN                                                               5

SEQ ID NO: 20            moltype = AA  length = 19
FEATURE                  Location/Qualifiers
REGION                   1..19
                         note = VH CDR2
source                   1..19
                         mol_type = protein
                         organism = synthetic construct
SEQUENCE: 20
FIGNKAYGYK IEYNSSVKG                                                19

SEQ ID NO: 21            moltype = AA  length = 6
FEATURE                  Location/Qualifiers
REGION                   1..6
                         note = VH CDR3
source                   1..6
                         mol_type = protein
                         organism = synthetic construct
SEQUENCE: 21
DGAFIY                                                              6

SEQ ID NO: 22            moltype = AA  length = 16
FEATURE                  Location/Qualifiers
REGION                   1..16
                         note = VH CDR1
source                   1..16
                         mol_type = protein
                         organism = synthetic construct
SEQUENCE: 22
RSSQSLVHSN GNTYLH                                                   16

SEQ ID NO: 23            moltype = AA  length = 7
FEATURE                  Location/Qualifiers
REGION                   1..7
                         note = VL CDR2
source                   1..7
                         mol_type = protein
                         organism = synthetic construct
SEQUENCE: 23
KVSNRFS                                                             7

SEQ ID NO: 24            moltype = AA  length = 9
FEATURE                  Location/Qualifiers
REGION                   1..9
                         note = VL CDR3
source                   1..9
                         mol_type = protein
                         organism = synthetic construct
SEQUENCE: 24
SQSTHIPYT                                                           9

SEQ ID NO: 25            moltype = AA  length = 30
FEATURE                  Location/Qualifiers
```

```
REGION                  1..30
                        note = VH FR1
source                  1..30
                        mol_type = protein
                        organism = synthetic construct
SEQUENCE: 25
EVKLVESGGG LVQPGDSLRL SCATSGFTFN                                      30

SEQ ID NO: 26           moltype = AA  length = 14
FEATURE                 Location/Qualifiers
REGION                  1..14
                        note = VH FR2
source                  1..14
                        mol_type = protein
                        organism = synthetic construct
SEQUENCE: 26
WVRQPPGKAL EWVA                                                       14

SEQ ID NO: 27           moltype = AA  length = 32
FEATURE                 Location/Qualifiers
REGION                  1..32
                        note = VH FR3
source                  1..32
                        mol_type = protein
                        organism = synthetic construct
SEQUENCE: 27
RFTISRDDSQ SFLYLQLNTL RSEDSATYYC AR                                   32

SEQ ID NO: 28           moltype = AA  length = 11
FEATURE                 Location/Qualifiers
REGION                  1..11
                        note = VH FR4
source                  1..11
                        mol_type = protein
                        organism = synthetic construct
SEQUENCE: 28
WGQGTVVTVS A                                                          11

SEQ ID NO: 29           moltype = AA  length = 23
FEATURE                 Location/Qualifiers
REGION                  1..23
                        note = VL FR1
source                  1..23
                        mol_type = protein
                        organism = synthetic construct
SEQUENCE: 29
DVVMTQTPLS LPVSLGDQAS ISC                                             23

SEQ ID NO: 30           moltype = AA  length = 15
FEATURE                 Location/Qualifiers
REGION                  1..15
                        note = VL FR2
source                  1..15
                        mol_type = protein
                        organism = synthetic construct
SEQUENCE: 30
WYLQKPGQSP KLLIY                                                      15

SEQ ID NO: 31           moltype = AA  length = 32
FEATURE                 Location/Qualifiers
REGION                  1..32
                        note = VL FR3
source                  1..32
                        mol_type = protein
                        organism = synthetic construct
SEQUENCE: 31
GVPDRFSGSG SGSDFTLKIS RVEAEDLGVY FC                                   32

SEQ ID NO: 32           moltype = AA  length = 10
FEATURE                 Location/Qualifiers
REGION                  1..10
                        note = VL FR4
source                  1..10
                        mol_type = protein
                        organism = synthetic construct
SEQUENCE: 32
FGGGTELEIR                                                            10

SEQ ID NO: 33           moltype = AA  length = 117
```

```
FEATURE               Location/Qualifiers
REGION                1..117
                      note = VH chain
source                1..117
                      mol_type = protein
                      organism = synthetic construct
SEQUENCE: 33
EVKLVESGGG LVQPGDSLRL SCATSGFTFN DHYMNWVRQP PGKALEWVAF IGNKAYGYKI   60
EYNSSVKGRF TISRDDSQSF LYLQLNTLRS EDSATYYCAR DGAFIYWGQG TVVTVSA     117

SEQ ID NO: 34         moltype = AA   length = 112
FEATURE               Location/Qualifiers
REGION                1..112
                      note = VL chain
source                1..112
                      mol_type = protein
                      organism = synthetic construct
SEQUENCE: 34
DVVMTQTPLS LPVSLGDQAS ISCRSSQSLV HSNGNTYLHW YLQKPGQSPK LLIYKVSNRF   60
SGVPDRFSGS GSGSDFTLKI SRVEAEDLGV YFCSQSTHIP YTFGGGTELE IR         112

SEQ ID NO: 35         moltype = AA   length = 441
FEATURE               Location/Qualifiers
REGION                1..441
                      note = Heavy chain
source                1..441
                      mol_type = protein
                      organism = synthetic construct
SEQUENCE: 35
EVKLVESGGG LVQPGDSLRL SCATSGFTFN DHYMNWVRQP PGKALEWVAF IGNKAYGYKI   60
EYNSSVKGRF TISRDDSQSF LYLQLNTLRS EDSATYYCAR DGAFIYWGQG TVVTVSAAKT  120
TPPSVYPLAP GSAAQTNSMV TLGCLVKGYF PEPVTVTWNS GSLSSGVHTF PAVLQSDLYT  180
LSSSVTVPSS TWPSETVTCN VAHPASSTKV DKKIVPRDCG CKPCICTVPE VSSVFIFPPK  240
PKDVLTITLT PKVTCVVVDI SKDDPEVQFS WFVDDVEVHT AQTQPREEQF NSTFRSVSEL  300
PIMHQDWLNG KEFKCRVNSA AFPAPIEKTI SKTKGRPKAP QVYTIPPPKE QMAKDKVSLT  360
CMITDFFPED ITVEWQWNGQ PAENYKNTQP IMDTDGSYFV YSKLNVQKSN WEAGNTFTCS  420
VLHEGLHNHH TEKSLSHSPG K                                           441

SEQ ID NO: 36         moltype = AA   length = 219
FEATURE               Location/Qualifiers
REGION                1..219
                      note = Light chain
source                1..219
                      mol_type = protein
                      organism = synthetic construct
SEQUENCE: 36
DVVMTQTPLS LPVSLGDQAS ISCRSSQSLV HSNGNTYLHW YLQKPGQSPK LLIYKVSNRF   60
SGVPDRFSGS GSGSDFTLKI SRVEAEDLGV YFCSQSTHIP YTFGGGTELE IRRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                        219

SEQ ID NO: 37         moltype = AA   length = 5
FEATURE               Location/Qualifiers
REGION                1..5
                      note = VH CDR1
source                1..5
                      mol_type = protein
                      organism = synthetic construct
SEQUENCE: 37
DTYMH                                                               5

SEQ ID NO: 38         moltype = AA   length = 17
FEATURE               Location/Qualifiers
REGION                1..17
                      note = VH CDR2
source                1..17
                      mol_type = protein
                      organism = synthetic construct
SEQUENCE: 38
RIDPANGNTK YDPKFQG                                                 17

SEQ ID NO: 39         moltype = AA   length = 13
FEATURE               Location/Qualifiers
REGION                1..13
                      note = VH CDR3
source                1..13
                      mol_type = protein
                      organism = synthetic construct
SEQUENCE: 39
```

-continued

```
NRAYYGNYYA MDY                                                       13

SEQ ID NO: 40          moltype = AA  length = 17
FEATURE                Location/Qualifiers
REGION                 1..17
                       note = VL CDR1
source                 1..17
                       mol_type = protein
                       organism = synthetic construct
SEQUENCE: 40
KSSQSLLNSR NQKNYLT                                                   17

SEQ ID NO: 41          moltype = AA  length = 7
FEATURE                Location/Qualifiers
REGION                 1..7
                       note = VL CDR2
source                 1..7
                       mol_type = protein
                       organism = synthetic construct
SEQUENCE: 41
WASTRES                                                              7

SEQ ID NO: 42          moltype = AA  length = 9
FEATURE                Location/Qualifiers
REGION                 1..9
                       note = VL CDR3
source                 1..9
                       mol_type = protein
                       organism = synthetic construct
SEQUENCE: 42
QNDYSYPFT                                                            9

SEQ ID NO: 43          moltype = AA  length = 30
FEATURE                Location/Qualifiers
REGION                 1..30
                       note = VH FR1
source                 1..30
                       mol_type = protein
                       organism = synthetic construct
SEQUENCE: 43
EVQLQQSGAE LVKPGASVKL SCTASGFNIK                                     30

SEQ ID NO: 44          moltype = AA  length = 14
FEATURE                Location/Qualifiers
REGION                 1..14
                       note = VH FR2
source                 1..14
                       mol_type = protein
                       organism = synthetic construct
SEQUENCE: 44
WVKQRPEQGL EWIG                                                      14

SEQ ID NO: 45          moltype = AA  length = 32
FEATURE                Location/Qualifiers
REGION                 1..32
                       note = VH FR3
source                 1..32
                       mol_type = protein
                       organism = synthetic construct
SEQUENCE: 45
KATITPDTSS TTAYLQLSSL TSEDTAVYYC AR                                  32

SEQ ID NO: 46          moltype = AA  length = 11
FEATURE                Location/Qualifiers
REGION                 1..11
                       note = VH FR4
source                 1..11
                       mol_type = protein
                       organism = synthetic construct
SEQUENCE: 46
WGQGTSVTVS S                                                         11

SEQ ID NO: 47          moltype = AA  length = 23
FEATURE                Location/Qualifiers
REGION                 1..23
                       note = VL FR1
source                 1..23
                       mol_type = protein
                       organism = synthetic construct
```

-continued

```
SEQUENCE: 47
DIVMTQSPSS LTVTAGEKVT MSC                                          23

SEQ ID NO: 48          moltype = AA  length = 15
FEATURE                Location/Qualifiers
REGION                 1..15
                       note = VL FR2
source                 1..15
                       mol_type = protein
                       organism = synthetic construct
SEQUENCE: 48
WYQQKPGQPP KLLIY                                                   15

SEQ ID NO: 49          moltype = AA  length = 32
FEATURE                Location/Qualifiers
REGION                 1..32
                       note = VL FR3
source                 1..32
                       mol_type = protein
                       organism = synthetic construct
SEQUENCE: 49
GVPDRFTGSG FGTDFTLAIS SVQAEDLAVY YC                                32

SEQ ID NO: 50          moltype = AA  length = 10
FEATURE                Location/Qualifiers
REGION                 1..10
                       note = VL FR4
source                 1..10
                       mol_type = protein
                       organism = synthetic construct
SEQUENCE: 50
FGSGTKLEIK                                                         10

SEQ ID NO: 51          moltype = AA  length = 122
FEATURE                Location/Qualifiers
REGION                 1..122
                       note = VH chain
source                 1..122
                       mol_type = protein
                       organism = synthetic construct
SEQUENCE: 51
EVQLQQSGAE LVKPGASVKL SCTASGFNIK DTYMHWVKQR PEQGLEWIGR IDPANGNTKY  60
DPKFQGKATI TPDTSSTTAY LQLSSLTSED TAVYYCARNR AYYGNYYAMD YWGQGTSVTV  120
SS                                                                122

SEQ ID NO: 52          moltype = AA  length = 113
FEATURE                Location/Qualifiers
REGION                 1..113
                       note = VL chain
source                 1..113
                       mol_type = protein
                       organism = synthetic construct
SEQUENCE: 52
DIVMTQSPSS LTVTAGEKVT MSCKSSQSLL NSRNQKNYLT WYQQKPGQPP KLLIYWASTR  60
ESGVPDRFTG SGFGTDFTLA ISSVQAEDLA VYYCQNDYSY PFTFGSGTKL EIK         113

SEQ ID NO: 53          moltype = AA  length = 458
FEATURE                Location/Qualifiers
REGION                 1..458
                       note = Heavy chain
source                 1..458
                       mol_type = protein
                       organism = synthetic construct
SEQUENCE: 53
EVQLQQSGAE LVKPGASVKL SCTASGFNIK DTYMHWVKQR PEQGLEWIGR IDPANGNTKY  60
DPKFQGKATI TPDTSSTTAY LQLSSLTSED TAVYYCARNR AYYGNYYAMD YWGQGTSVTV  120
SSAKTTPPSV YPLAPGCGDT TGSSVTLGCL VKGYFPESVT VTWNSGSLSS SVHTFPALLQ  180
SGLYTMSSSV TVPSSTWPSQ TVTCSVAHPA SSTTVDKKLE PSGPISTINP CPPCKECHKC  240
PAPNLEGGPS VFIFPPNIKD VLMISLTPKV TCVVVDVSED DPDVQISWFV NNVEVHTAQT  300
QTHREDYNST IRVVSTLPIQ HQDWMSGKEF KCKVNNKDLP SPIERTISKI KGLVRAPQVY  360
ILPPPAEQLS RKDVSLTCLV VGFNPGDISV EWTSNGHTEE NYKDTAPVLD SDGSYFIYSK  420
LNMKTSKWEK TDSFSCNVRH EGLKNYYLKK TISRSPGK                          458

SEQ ID NO: 54          moltype = AA  length = 220
FEATURE                Location/Qualifiers
REGION                 1..220
                       note = Light chain
source                 1..220
                       mol_type = protein
```

-continued

```
                    organism = synthetic construct
SEQUENCE: 54
DIVMTQSPSS LTVTAGEKVT MSCKSSQSLL NSRNQKNYLT WYQQKPGQPP KLLIYWASTR   60
ESGVPDRFTG SGFGTDFTLA ISSVQAEDLA VYYCQNDYSY PFTFGSGTKL EIKRADAAPT  120
VSIFPPSSEQ LTSGGASVVC FLNNFYPKDI NVKWKIDGSE RQNGVLNSWT DQDSKDSTYS  180
MSSTLTLTKD EYERHNSYTC EATHKTSTSP IVKSFNRNEC                        220
```

DETERMINATION OF CANINE TK1 PROTEIN LEVELS

The sequence listing submitted herewith, entitled Nov-7-2025 Sequence Listing.xml, created Nov. 7, 2025 and having a size of 73,805 bytes, is incorporated herein by reference.

TECHNICAL FIELD

The present embodiments generally relate to determination of TK1 protein levels, and in particular to a kit and methods involving the use of monoclonal anti-TK1 antibodies for determining canine TK1 protein levels.

BACKGROUND

Dogs are frequently affected with various neoplastic diseases like lymphomas, leukemias and mammary tumors. Lymphomas are the most common form of hematological tumors and accounts for 5% of all cancers in dog. The annual incidence has been estimated to 13 to 40 cases per 100,000 dogs. Canine lymphoma is similar to human non-Hodgkin's lymphoma in terms of genetic and environmental factors that contribute to disease progression. Early stage diagnosis in combination with effective chemotherapy can control the malignancy. Several proliferation markers including argyrophilic nucleolar organizing regions (AgNORs), proliferation cell nuclear antigen (PCNA) and Ki-67 have been investigated as prognostic markers in canine lymphoma, but their usage is limited to immunohistochemistry. Serum lactate dehydrogenase (LDH) was also investigated as a marker for monitoring canine lymphomas, but LDH is upregulated in diseases other than malignancies and, thus, has a limited clinical value (von Euler et al., 2006).

Tumor progression is dependent on cell proliferation and proliferation markers are valuable in order to detect tumor diseases at an early stage. Thymidine kinase 1 (TK1) is one of the biomarkers that is released into the blood during uncontrolled cell growth. TK1 converts deoxythymidine (dT) to deoxythymidine monophosphate (dTMP), which is eventually incorporated into DNA in proliferating cells. TK1 activity is tightly associated with the cell cycle and reaches a peak in S-phase, declines rapidly in G2, and is degraded by specific mechanisms in M phase.

Serum TK1 (STK1) activity measurements is an established tool for diagnosis and monitoring of lymphomas and leukemia's in human medicine. STK1 activity is measured by using several enzymatic assays e.g., TK radioenzymatic assay (TK-RIA), such as PROLIFIGEN®, or TK chemiluminescent immune assay (TK-CLIA), such as LIAISON® TK, where a thymidine substrate analogue, like $^{125}$I-iododeoxyuridine or azidothymidine (AZT), is phosphorylated into the corresponding monophosphate. Studies have shown that both TK-REA and TK-CLIA assays provide valuable information for prognosis and treatment monitoring of canine hematological tumors. A study, using the natural substrate [$^{3}$H]-dThd (deoxy thymidine) instead of substrate analogues, showed that this assay was equally sensitive as the TK-REA and TK-CLIA assays and could be used for monitoring canine lymphomas (Sharif et al., 2012).

Presently, there are no immunochemical methods available for canine oncology studies. However, studies have been performed using an immunoaffinity assay based on antibodies against the dog TK1 C-terminal (Kiran Kumar et al., 2013; Jagarlamudi et al., 2014). This allowed determination of serum TK1 protein levels in canine subjects with various malignancies and concluded that the TK1 protein assay was more sensitive than TK1 activity assay for differentiation of canine solid tumors from healthy dogs. Kiran Kumar 2010 disclosed production of anti-dog TK1 antibodies for detection of serum TK1. The antibodies were produced by immunizing rabbits with a 28 amino acid long peptide corresponding to amino acids 196 to 223 in dog TK1. A sandwich ELISA for quantification of TK1 protein levels in sera from dogs is presented in Jagarlamudi et al., 2015. The sandwich ELISA used polyclonal anti-dog TK1 antibodies raised against a 16 amino acid long synthetic peptide from the C-terminal region of dog TK1 corresponding to amino acids 215 to 231 in dog TK1 and a monoclonal anti-human TK1 antibody produced against the long lasso shaped loop of human TK1 corresponding to amino acids 161 to 183 in human TK1.

There is, however, still a need for a clinically acceptable technique for measuring TK1 protein levels in canine subjects.

SUMMARY

It is a general objective to provide a kit and methods for measuring TK1 protein levels in dogs.

This and other objectives are met by embodiments as defined herein.

An aspect of the embodiments relates to a kit for determining a level of canine TK1 protein in a sample. The kit comprises a first monoclonal antibody, or a fragment thereof, immobilized to a support or intended to be immobilized to the support and a second monoclonal antibody, or a fragment thereof. One of the first monoclonal antibody, or the fragment thereof, and the second monoclonal antibody, or the fragment thereof, has specificity for a peptide consisting of an amino acid sequence from an active site of TK1. Furthermore, this monoclonal antibody, or the fragment thereof, has a VH CDR1 having amino acid sequence SEQ ID NO: 19, a VH CDR2 having amino acid sequence SEQ ID NO: 20, a VH CDR3 having amino acid sequence SEQ ID NO: 21, a variable light, VL, CDR1 having amino acid sequence SEQ ID NO: 22, a VL CDR2 having amino acid sequence SEQ ID NO: 23 and a VL CDR3 having amino acid sequence SEQ ID NO: 24. The other of the first monoclonal antibody, or the fragment thereof, and the second monoclonal antibody, or the fragment thereof, has specificity for a peptide consisting of an amino acid sequence from the C-terminal region of canine TK1. This monoclonal antibody, or the fragment thereof, has a VH CDR1 having amino acid sequence SEQ ID NO: 37, a VH CDR2 having amino acid sequence SEQ ID NO: 38, a VH CDR3 having amino acid sequence SEQ ID NO: 39, a VL CDR1 having amino acid sequence SEQ ID NO: 40, a VL CDR2 having amino acid sequence SEQ ID NO: 41 and a VL CDR3 having amino acid sequence SEQ ID NO: 42.

Another aspect of the embodiments relates to a method for determining a level of canine TK1 protein in a sample. The method comprises contacting the sample with a first monoclonal antibody, or a fragment thereof, and a second monoclonal antibody, or a fragment thereof, of the kit as defined above. The method also comprises detecting an amount of bound second antibody. The method further comprises determining the level of canine TK1 protein in the sample based on the detected amount of bound second antibody.

The embodiments enable determining TK1 protein levels in canine subjects, i.e., dogs. The kit and methods of the embodiments are easy to perform, fast and as sensitive and specific as existing TK1 activity assays. The kit and methods are furthermore far more sensitive than TK1 activity assays in differentiating healthy dogs from dogs suffering from solid tumors.

BRIEF DESCRIPTION OF THE DRAWINGS

The embodiments, together with further objects and advantages thereof, may best be understood by making reference to the following description taken together with the accompanying drawings, in which:

FIGS. 4A and 4B show immunoprecipitation with DYNABEADS®. Recombinant canine TK1 at 5 and 2.5 ng concentration and sera from different malignancies were incubated at room temperature with 4 pg/ml of mAb1 diluted in TBST containing 2% of BSA (FIG. 4A) and 4 pg/ml mAb 2 (FIG. 4B). The results were represented as the percentage of TK1 that was not bound to the magnetic beads.

(FIG. 5A) Log serum thymidine kinase protein measured in healthy dogs (n=118) and dogs with different malignancies (n=159), the lines represent median. (FIG. 5B) Receiver operating characteristic (ROC) curve of STK1 protein values for distinguishing between dogs with different malignancies and healthy dogs. (FIG. 5C) Log STK1 activity distribution in sera from healthy dogs (n=118)

and sera from dogs with different malignancies (n=159), error bars represent median. (FIG. 5D) ROC curve analysis of the STK1 activity levels.

FIGS. 6A-6D show STK1 distribution in different lymphoma group. (FIG. 6A) Log STK1 protein distribution in sera from healthy dogs (n=118) and dogs with lymphoma (n=75), the lines represent median. (FIG. 6B) ROC curve of STK1 protein values for distinguishing between dogs with lymphoma and healthy dogs. (FIG. 6C) Log STK1 activity levels in sera from healthy dogs and dogs with lymphoma (FIG. 6D) ROC curve analysis of the STK1 activity levels.

FIGS. 8A-8D show dual monoclonal TK1 ELISA in the carcinomas group. (FIG. 8A) Log serum thymidine kinase protein measured in healthy dogs (n=118) and dogs with carcinomas (Hemangiosarcoma 18, Histiocytic sarcoma 28, malignant mammary tumors 18, and other carcinoma e.g., melanoma, squamous cell carcinoma, renal carcinoma, liver and spleen carcinoma), the lines represent median. (FIG. 8B) ROC curve of STK1 protein values for distinguishing between dogs with different carcinomas and healthy dogs. (FIG. 8C) Log STK1 activity distribution in sera from healthy dogs (n=118) and sera from dogs with different malignancies (n=84), error bars represent median. (FIG. 8D) ROC curve analysis of the STK1 activity levels.

DETAILED DESCRIPTION

The present embodiments generally relate to determination of canine TK1 protein levels, and in particular to a kit and methods involving the use of monoclonal anti-TK1 antibodies for determining canine TK1 protein levels.

Figure 1:
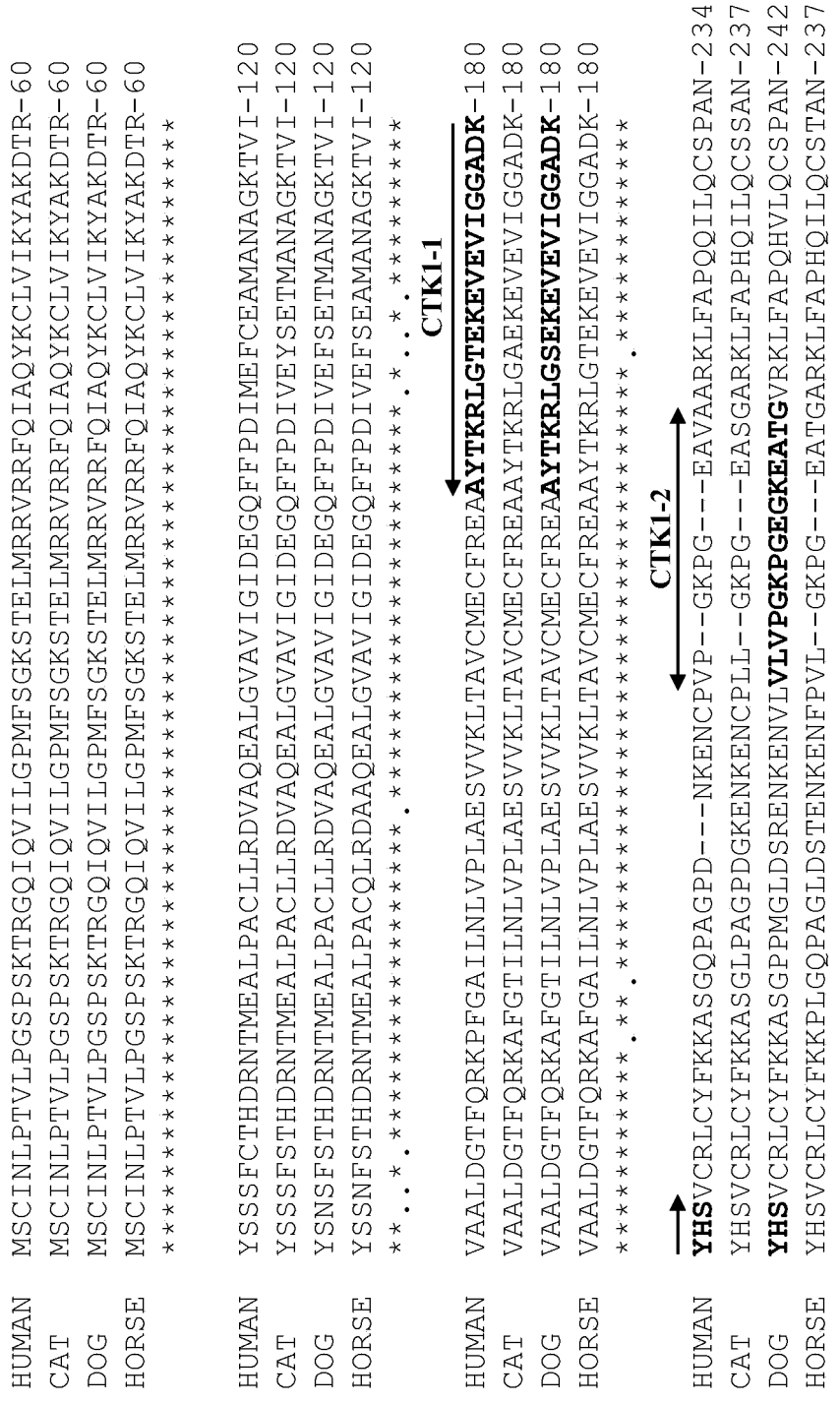
FIG. 1 illustrates amino acid sequence alignments of human TK1 (GenBank accession no. KO_2582; SEQ ID NO: 2), dog TK1 (also referred to as canine TK1 herein, GenBank accession no. XM_540461; SEQ ID NO: 1), cat TK1 (also referred to as feline TK1 herein, GenBank accession no. XP_3997286.2; SEQ ID NO: 3) and horse TK1 (also referred to as equine TK1 herein, GenBank accession no. XP_1491131.2; SEQ ID NO: 4) deduced amino acid sequences. Monoclonal antibodies raised against the active site region of human TK1 (CTK1-1, amino acids 161-183 in human TK1, AYTKRLGTEKEVEVIGGADKYHS (SEQ ID NO: 5)) and against the C-terminal region of dog TK1 (CTK1-2, amino acids 211-225 in dog TK1, VLVPGKPGEGKEATG (SEQ ID NO: 9)).

The crystal structure of human TK1 has been resolved and the major part of the enzyme, including the N-terminal region, is conserved in humans, dogs, cats and horses except for a few residues, see FIG. 1 and SEQ ID NO: 1 representing dog TK1 (canine TK1), SEQ ID NO: 2 representing human TK1, SEQ ID NO: 3 representing cat TK1 (feline TK1) and SEQ ID NO: 4 representing horse TK1 (equine TK1). For instance, human TK1 sequence shows 88.5% similarity with dog TK1 but a significant sequence diversity (9.1%) is found in the C-terminal region.

An aspect of the embodiments relates to a kit for determining a level of canine TK1 protein in a sample. The kit comprises a first monoclonal antibody, or a fragment thereof, immobilized to a support or intended to be immobilized to the support and a second monoclonal antibody, or a fragment thereof. According to the embodiments, one of the first monoclonal antibody, or the fragment thereof, and the second monoclonal antibody, or the fragment thereof, has specificity for a peptide consisting of an amino acid sequence from an active site of TK1. The other of the first monoclonal antibody, or the fragment thereof, and second monoclonal antibody, or the fragment thereof, has specificity for a peptide consisting of an amino acid sequence from the C-terminal region of canine TK1.

The kit is in particular suitable for determining the level of canine serum TK1 (STK1) protein in a sample, preferably a body sample, and in particular a body fluid sample from a canine subject.

The peptide consisting of the amino acid sequence from the C-terminal regional of canine TK1 is preferably a peptide selected from a portion of the canine TK1 ranging from amino acid position 200 to the end of the canine TK1, i.e., amino acid position 242. In a particular embodiment, the peptide is selected from a portion of the canine TK1 protein ranging from amino acid position 205, preferably 210 and more preferably 211, to amino acid position 240, preferably 235 and more preferably 230.

The peptide is preferably an N-mer, wherein N is an integer within a range of 10 and 25, preferably 10 to 20 and more preferably 15, 16 or 17.

The peptide preferably consists of N consecutive amino acids in the C-terminal region of the canine TK1 protein. N is as defined above.

At least one additional amino acid, such as a cysteine residue, may be added to the N-terminal or C-terminal, preferably the N-terminal, of the peptide for use as coupling to other molecules, such as carrier proteins.

In an embodiment, the peptide consisting of an amino acid sequence from the C-terminal region of canine has an amino acid sequence corresponding to amino acid positions 211 to 225 in canine TK1, see FIG. 1, i.e., has amino acid sequence of VLVPGKPGEGKEATG (SEQ ID NO: 9). The corresponding amino acid sequence with the added N-terminal cysteine residue is CVLVPGKPGEGKEATG (SEQ ID NO: 10).

The peptide consisting of an amino acid sequence from an active site of TK1 is preferably a peptide selected from a portion of TK1 ranging from amino acid position 150 to amino acid position 190. In a particular embodiment, the peptide is selected from a portion of TK1 ranging from amino acid position 155, preferably 160 and more preferably 161, to amino acid position 185, preferably 183.

The peptide is preferably an M-mer, wherein M is an integer within a range of 10 and 40, preferably 20 to and more preferably 23 or 24.

The peptide preferably consists of M consecutive amino acids in the active site of the TK1 protein. M is as defined above.

This portion representing the active site of TK1 shows very high levels of homology between different species, such as between human, canine, feline and equine TK1 as shown in FIG. 1. For instance, there is only a difference in a single amino acid position between human TK1 and canine TK1 within the portion extending from amino acid position 150 to amino acid position 190.

Hence, the peptide could consist of an amino acid sequence from an active site of human TK1 or from canine TK1. Experimental data as presented herein shows that a monoclonal antibody that has specificity for a peptide consisting of an amino acid sequence from the active site of human TK1 binds specifically also to canine TK1.

At least one additional amino acid, such as a cysteine residue, may be added to the N-terminal or C-terminal, preferably the N-terminal, of the peptide for use as coupling to other molecules, such as carrier proteins.

In an embodiment, the peptide consisting of an amino acid sequence from the active site of TK1 has an amino acid sequence corresponding to amino acid positions 161 to 183 in human TK1, see FIG. 1, i.e., has amino acid sequence of AYTKRLGTEKEVEVIGGADKYHS (SEQ ID NO: 5). The corresponding amino acid sequence with the added N-terminal cysteine residue is CAYTKRLGTEKEVEVIGGAD-KYHS (SEQ ID NO: 6).

In another embodiment, the peptide consisting of an amino acid sequence from the active site of TK1 has an amino acid sequence corresponding to amino acid positions 161 to 183 in canine TK1, see FIG. 1, i.e., has amino acid sequence of AYTKRLGSEKEVEVIGGADKYHS (SEQ ID NO: 7). The corresponding amino acid sequence with the added N-terminal cysteine residue is CAYTKRLGSEKEV-EVIGGADKYHS (SEQ ID NO: 8).

According to the invention, the kit for determining the level of canine TK1 protein in a sample comprises the first monoclonal antibody, or the fragment thereof, immobilized to a support or intended to be immobilized to the support and the second monoclonal antibody, or the fragment thereof. One of the first and the second antibody has specificity for a peptide consisting of an amino acid sequence from the active site of TK1 and the other of the first antibody and the second antibody has specificity for a peptide consisting of an amino acid sequence from the C-terminal region of TK1.

In a particular embodiment, one of the first monoclonal antibody, or the fragment thereof, and the second monoclonal antibody, or the fragment thereof, has specificity for a peptide consisting of an amino acid sequence selected from a group consisting of SEQ ID NO: 5, SEQ ID NO: 6, SEQ ID NO: 7 and SEQ ID NO: 8 and the other of the first monoclonal antibody, or the fragment thereof, and the second monoclonal antibody, or the fragment thereof, has specificity for a peptide consisting of an amino acid sequence selected from a group consisting of SEQ ID NO: 9 and SEQ ID NO: 10. Particular combinations of the first and second monoclonal antibodies, or the fragments thereof, according to this embodiment, thus, involve a monoclonal antibody, or a fragment thereof, having specificity for a peptide consisting of an amino acid sequence consisting of SEQ ID NO: 5 and a monoclonal antibody, or a fragment thereof, having specificity for a peptide consisting of an amino acid sequence consisting of SEQ ID NO: 9, a monoclonal antibody, or a fragment thereof, having specificity for a peptide consisting of an amino acid sequence consisting of SEQ ID NO: 5 and an antibody having specificity for a peptide consisting of an amino acid sequence consisting of SEQ ID NO: 10, a monoclonal antibody, or a fragment thereof, having specificity for a peptide consisting of an amino acid sequence consisting of SEQ ID NO: 6 and a monoclonal antibody, or a fragment thereof, having specificity for a peptide consisting of an amino acid sequence consisting of SEQ ID NO: 9, a monoclonal antibody, or a fragment thereof, having specificity for a peptide consisting of an amino acid sequence consisting of SEQ ID NO: 6 and a monoclonal antibody, or a fragment thereof, having specificity for a peptide consisting of an amino acid sequence consisting of SEQ ID NO: 10, a monoclonal antibody, or a fragment thereof, having specificity for a peptide consisting of an amino acid sequence consisting of SEQ ID NO: 7 and a monoclonal antibody, or a fragment thereof, having specificity for a peptide consisting of an amino acid sequence consisting of SEQ ID NO: 9, a monoclonal antibody, or a fragment thereof, having specificity for a peptide consisting of an amino acid sequence consisting of SEQ ID NO: 7 and a monoclonal antibody, or a fragment thereof, having specificity for a peptide consisting of an amino acid sequence consisting of SEQ ID NO: 10, a monoclonal antibody, or a fragment thereof, having specificity for a peptide consisting of an amino acid sequence consisting of SEQ ID NO: 8 and a monoclonal antibody, or a fragment thereof, having specificity for a peptide consisting of an amino acid sequence consisting of SEQ ID NO: 9, and a monoclonal antibody, or a fragment thereof, having specificity for a peptide consisting of an amino acid sequence consisting of SEQ ID NO: 8 and a monoclonal antibody, or a fragment thereof, having specificity for a peptide consisting of an amino acid sequence consisting of SEQ ID NO: 10.

In a preferred embodiment, one of the first monoclonal antibody, or the fragment thereof, and the second monoclonal antibody, or the fragment thereof is the CTK1-1 (mAb1) antibody and the other of the first monoclonal antibody, or the fragment thereof, and the second monoclonal antibody, or the fragment thereof, is the CTK1-2 (mAb2) antibody.

One or both of the monoclonal antibodies may be an antibody fragment having specificity for the relevant peptide, i.e., an antigen-binding fragment of a monoclonal antibody. In such a case, the fragment can be selected from a group consisting of a single chain antibody, a Fv fragment, a scFv fragment, a Fab fragment, a F(ab')2 fragment, a Fab' fragment, a Fd fragment, a single-domain antibody (sdAb), a scFv-Fc fragment, and a di-scFv fragment.

In an embodiment, the monoclonal antibody, or a fragment thereof, having specificity for a peptide consisting of an amino acid sequence from an active site of TK1 has a variable heavy (VH) complementary determining region (CDR) 1 (CDR1) having amino acid sequence DHYMN (SEQ ID NO: 19), a VH CDR2 having amino acid sequence FIGNKAYGYKIEYNSSVKG (SEQ ID NO: 20), and a VH CDR3 having amino acid sequence DGAFIY (SEQ ID NO: 21). The monoclonal antibody, or the fragment thereof, also has a variable light (VL) CDR1 having amino acid sequence RSSQSLVHSNGNTYLH (SEQ ID NO: 22), a VL CDR2 having amino acid sequence KVSNRFS (SEQ ID NO: 23) and a VL CDR3 having amino acid sequence SQSTHIPYT (SEQ ID NO: 24).

Optionally, the monoclonal antibody, or the fragment thereof, may have a VH framework (FR) 1 (FR1) having amino acid sequence EVKLVESGGGLVQPGDSLRLS-CATSGFTFN (SEQ ID NO: 25), a VH FR2 having amino acid sequence WVRQPPGKALEWVA (SEQ ID NO: 26), a VH FR3 having amino acid sequence RFTISRDDSQSFLY-LQLNTLRSEDSATYYCAR (SEQ ID NO: 27) and a VH FR4 having amino acid sequence WGQGTVVTVSA (SEQ ID NO: 28). The monoclonal antibody, or the fragment thereof, may optionally also have a VL FR1 having amino acid sequence DVVMTQTPLSLPVSLGDQASISC (SEQ ID NO: 29), a VL FR2 having amino acid sequence WYLQKPGQSPKLLIY (SEQ ID NO: 30), a VL FR3 having amino acid sequence GVPDRFSGSGSGSDFTLKISRVEAEDLGVYFC (SEQ ID NO: 31) and a VL FR4 having amino acid sequence FGGGTELEIR (SEQ ID NO: 32).

In an optional embodiment, the monoclonal antibody, or the fragment thereof, has a variable heavy chain (VH FR1-VH CDR1-VH FR2-VH CDR2-VH FR3-VH CDR3-VH FR4) having amino acid sequence SEQ ID NO: 33:.

EVKLVESGGGLVQPGDSLRLSCATSGFTENDHYMNWVRQPPGKALEWVA
FIGNKAYGYKIEYNSSVKGRFTISRDDSQSFLYLQLNTLRSEDSATYYC
ARDGAFIYWGQGTVVTVSA

The monoclonal antibody, or the fragment thereof, optionally has a variable light chain (VL FR1-VL CDR1-VL FR2-VL CDR2-VL FR3-VL CDR3-VL FR4) having amino acid sequence SEQ ID NO: 34:

DVVMTQTPLSLPVSLGDQASISCRSSQSLVHSNGNTYLHWYLQKPGQSP
KLLIYKVSNRFSGVPDRFSGSGSGSDFTLKISRVEAEDLGVYFC**SQSTH
IPYT**FGGGTELEIR

In a particular embodiment, the monoclonal antibody has a heavy chain having amino acid sequence SEQ ID NO: 35:

EVKLVESGGGLVQPGDSLRLSCATSGFTENDHYMNWVRQPPGKALEWVA

FIGNKAYGYKIEYNSSVKGRFTISRDDSQSFLYLQLNTLRSEDSATYYC

ARDGAFIYWGQGTVVTVSAAKTTPPSVYPLAPGSAAQTNSMVTLGCLVK

GYFPEPVTVTWNSGSLSSGVHTFPAVLQSDLYTLSSSVTVPSSTWPSET

VTCNVAHPASSTKVDKKIVPRDCGCKPCICTVPEVSSVFIFPPKPKDVL

TITLTPKVTCVVVDISKDDPEVQFSWFVDDVEVHTAQTQPREEQFNSTE

RSVSELPIMHQDWLNGKEFKCRVNSAAFPAPIEKTISKTKGRPKAPQVY

TIPPPKEQMAKDKVSLTCMITDFFPEDITVEWQWNGQPAENYKNTQPIM

DTDGSYFVYSKLNVQKSNWEAGNTFTCSVLHEGLHNHHTEKSLSHSPGK

In a particular embodiment, the monoclonal antibody has a light chain having amino acid sequence SEQ ID NO: 36:

DVVMTQTPLSLPVSLGDQASISCRSSQSLVHSNGNTYLHWYLQKPGQSP

KLLIYKVSNRFSGVPDRESGSGSGSDFTLKISRVEAEDLGVYFCSQSTH

IPYTFGGGTELEIRRADAAPTVSIFPPSSEQLTSGGASVVCFLNNFYPK

DINVKWKIDGSERQNGVLNSWTDQDSKDSTYSMSSTLTLTKDEYERHNS

YTCEATHKTSTSPIVKSENRNEC

A monoclonal antibody according to these embodiments is denoted CTK1-1 (mAb1) herein. In an embodiment, the monoclonal antibody, or the fragment thereof, having specificity for a peptide consisting of an amino acid sequence from a C-terminal region of the canine TK1 has a CDR1 having amino acid sequence DTYMH (SEQ ID NO: 37), a VH CDR2 having amino acid sequence RIDPANGNT-KYDPKFQG (SEQ ID NO: 38), and a VH CDR3 having amino acid sequence NRAYYGNYYAMDY (SEQ ID NO: 39). The monoclonal antibody, or the fragment thereof, also has a VL CDR1 having amino acid sequence KSSQSLLN-SRNQKNYLT (SEQ ID NO: 40), a VL CDR2 having amino acid sequence WASTRES (SEQ ID NO: 41) and a VL CDR3 having amino acid sequence QNDYSYPFT (SEQ ID NO: 42).

Optionally, the monoclonal antibody, or the fragment thereof, may have a VH FR1 having amino acid sequence EVQLQQSGAELVKPGASVKLSCTASGFNIK (SEQ ID NO: 43), a VH FR2 having amino acid sequence WVKQRPEQGLEWIG (SEQ ID NO: 44), a VH FR3 having amino acid sequence KATITPDTSSTTAYLQLSSLT-SEDTAVYYCAR (SEQ ID NO: 45) and a VH FR4 having amino acid sequence WGQGTSVTVSS (SEQ ID NO: 46).

The monoclonal antibody, or the fragment thereof, may optionally also have a VL FR1 having amino acid sequence DIVMTQSPSSLTVTAGEKVTMSC (SEQ ID NO: 47), a VL FR2 having amino acid sequence WYQQKPGQPPKLLIY (SEQ ID NO: 48), a VL FR3 having amino acid sequence GVPDRFTGSGFGTDFT-LAISSVQAEDLAVYYC (SEQ ID NO: 49) and a VL FR4 having amino acid sequence FGSGTKLEIK (SEQ ID NO: 50).

In an optional embodiment, the monoclonal antibody, or the fragment thereof, has a variable heavy chain (VH FR1-VH CDR1-VH FR2-VH CDR2-VH FR3-VH CDR3-VH FR4) having amino acid sequence SEQ ID NO: 51:

```
EVQLQQSGAELVKPGASVKLSCTASGENIKDTYMHWVKQRPEQGLEWIG
RIDPANGNTKYDPKFQGKATITPDTSSTTAYLQLSSLTSEDTAVYYCAR
NRAYYGNYYAMDYWGQGTSVTVSS
```

The monoclonal antibody, or the fragment thereof, optionally has a variable light chain (VL FR1-VL CDR1-VL FR2-VL CDR2-VL FR3-VL CDR3-VL FR4) having amino acid sequence SEQ ID NO: 52:

```
DIVMTQSPSSLTVTAGEKVTMSCKSSQSLLNSRNQKNYLTWYQQKPGQP
PKLLIYWASTRESGVPDRFTGSGFGTDFTLAISSVQAEDLAVYYCQNDY
SYPFTFGSGTKLEIK
```

In a particular embodiment, the monoclonal antibody has a heavy chain having amino acid sequence SEQ ID NO: 53:

```
EVQLQQSGAELVKPGASVKLSCTASGENIKDTYMHWVKQRPEQGLEWIG

RIDPANGNTKYDPKFQGKATITPDTSSTTAYLQLSSLTSEDTAVYYCAR

NRAYYGNYYAMDYWGQGTSVTVSSAKTTPPSVYPLAPGCGDTTGSSVTL

GCLVKGYFPESVTVTWNSGSLSSSVHTFPALLQSGLYTMSSSVTVPSST

WPSQTVTCSVAHPASSTTVDKKLEPSGPISTINPCPPCKECHKCPAPNL

EGGPSVFIFPPNIKDVLMISLTPKVTCVVVDVSEDDPDVQISWFVNNVE

VHTAQTQTHREDYNSTIRVVSTLPIQHQDWMSGKEFKCKVNNKDLPSPI

ERTISKIKGLVRAPQVYILPPPAEQLSRKDVSLTCLVVGENPGDISVEW

TSNGHTEENYKDTAPVLDSDGSYFIYSKLNMKTSKWEKTDSFSCNVRHE

GLKNYYLKKTISRSPGK
```

In a particular embodiment, the monoclonal antibody has a light chain having amino acid sequence SEQ ID NO: 54:

```
DIVMTQSPSSLTVTAGEKVTMSCKSSQSLLNSRNQKNYLTWYQQKPGQP

PKLLIYWASTRESGVPDRFTGSGFGTDFTLAISSVQAEDLAVYYCQNDY

SYPFTFGSGTKLEIKRADAAPTVSIFPPSSEQLTSGGASVVCFLNNFYP

KDINVKWKIDGSERQNGVLNSWTDQDSKDSTYSMSSTLTLTKDEYERHN

SYTCEATHKTSTSPIVKSENRNEC
```

A monoclonal antibody according to these embodiments is denoted CTK1-2 (mAb2) herein. A monoclonal antibody, or a fragment thereof, having specificity for a peptide means that the monoclonal antibody, or the fragment thereof, binds specifically to the peptide.

The specificity of a monoclonal antibody, or a fragment thereof, can be determined based on affinity and/or avidity. The affinity, represented by the equilibrium constant for the dissociation of an antigen with the monoclonal antibody, or the fragment thereof, ($K_D$), is a measure for the binding strength between an antigenic determinant and an antigen-binding site on the monoclonal antibody, or the fragment thereof.

The lesser the value of $K_D$, the stronger the binding strength between the antigenic determinant and the monoclonal antibody, or the fragment thereof. Alternatively, the affinity can also be expressed as the affinity constant ($K_A$), which is $1/K_D$. As will be clear to the skilled person, affinity can be determined in a manner known per se, depending on the specific antigen of interest.

Avidity is the measure of the strength of binding between the monoclonal antibody, or the fragment thereof, and the pertinent antigen. Avidity is related to both the affinity between an antigenic determinant and its antigen binding site on the monoclonal antibody, or the fragment thereof, and the number of pertinent binding sites present on the monoclonal antibody, or the fragment thereof.

Typically, monoclonal antibodies, or fragments thereof, will bind to their antigen with a dissociation constant ($K_D$) of $10^{-7}$ to $10^{12}$ moles/liter (M) or less, and preferably $10^{-8}$ to $10^{-12}$ M or less and more preferably $10^{-9}$ to $10^{-12}$ M, i.e., with an association constant ($K_A$) of $10^7$ to $10^{-12}$ $M^{-1}$ or more, and preferably $10^8$ to $10^{12}$ $M^{-1}$ or more and more preferably $10^9$ to $10^{12}$ $M^{-1}$.

Generally, any $K_D$ value greater than $10^{-4}$ M (or any $K_A$ value lower than $10^4$ $M^{-1}$) is generally considered to indicate non-specific binding.

Preferably, a monoclonal antibody, or a fragment thereof, of the embodiments will bind to the serum form and/or recombinant form of canine TK1 with an affinity less than 500 nM, preferably less than 200 nM, more preferably less than 10 nM, such as less than 5 nM, preferably equal to or less than 2.5 nM, such as equal to or less than 1 nM.

In a particular embodiment, the kit is a sandwich assay kit. This means that the kit uses monoclonal antibodies, or fragments thereof, binding to different epitopes of canine TK1 protein so that both the first and second monoclonal antibodies, or the fragments thereof, can simultaneously bind to the same canine TK1 molecule or complex.

In a particular embodiment, the kit is an Enzyme-Linked Immunosorbent Assay (ELISA) kit and preferably a sandwich ELISA.

A sandwich ELISA can be used to detect cellular and/or serum canine TK1 protein, in particular serum canine TK1 protein, in a sample by preparing a surface of a support, such as a solid support, to which the first monoclonal antibody, or the fragment thereof, is bound as so-called capture antibody. In a preferred embodiment, a known quantity of the first monoclonal antibody, or the fragment thereof, is bound to the surface of the support. Any non-specific binding sites on the surface are optionally but preferably blocked. The sample is then applied to the surface so that any canine TK1 protein present therein will be captured by the immobilized first monoclonal antibodies, or the fragments thereof. Unbound material is preferably removed by one or multiple washing steps. The second monoclonal antibody, or the fragment thereof, typically denoted detection antibody, is then added and is allowed to bind to any canine TK1 protein captured by the first monoclonal antibody, or the fragment thereof.

The amount of bound second monoclonal antibody, or the fragment thereof, is then determined by direct or indirect detection methods. For instance, a label or enzyme can be attached directly to the second monoclonal antibody, or the fragment thereof, or indirectly via a link, such as a biotin-streptavidin or a biotin-avidin link. It is, alternatively, possible to use a secondary antibody that is labeled or connected to an enzyme and binds specifically to the second monoclonal antibody, or the fragment thereof.

Hence, in an embodiment the second monoclonal antibody, or the fragment thereof, has a covalently attached biotin. Alternatively, the second monoclonal antibody, or the fragment thereof, has a covalently attached streptavidin or avidin.

The kit preferably also comprises a horseradish peroxidase (HRP) labeled streptavidin or a HRP labeled avidin. Alternatively, the kit also comprises a HRP labeled biotin. The kit also comprises a HRP substrate, such as a 3,3',5,5'-tetramethylbenzidine (TMB) substrate, a 3,3'-diaminobenzidine (DAB) substrate or a 2,2'-azino-bis(3-ethylbenzothiazoline-6-sulphonic acid (ABTS) substrate. In such a case, the level of canine TK1 protein in the sample can be determined by spectrophotometric methods that detect the conversion of the chromogenic substrate by HRP into a colored product that is detectable.

Figure 2:
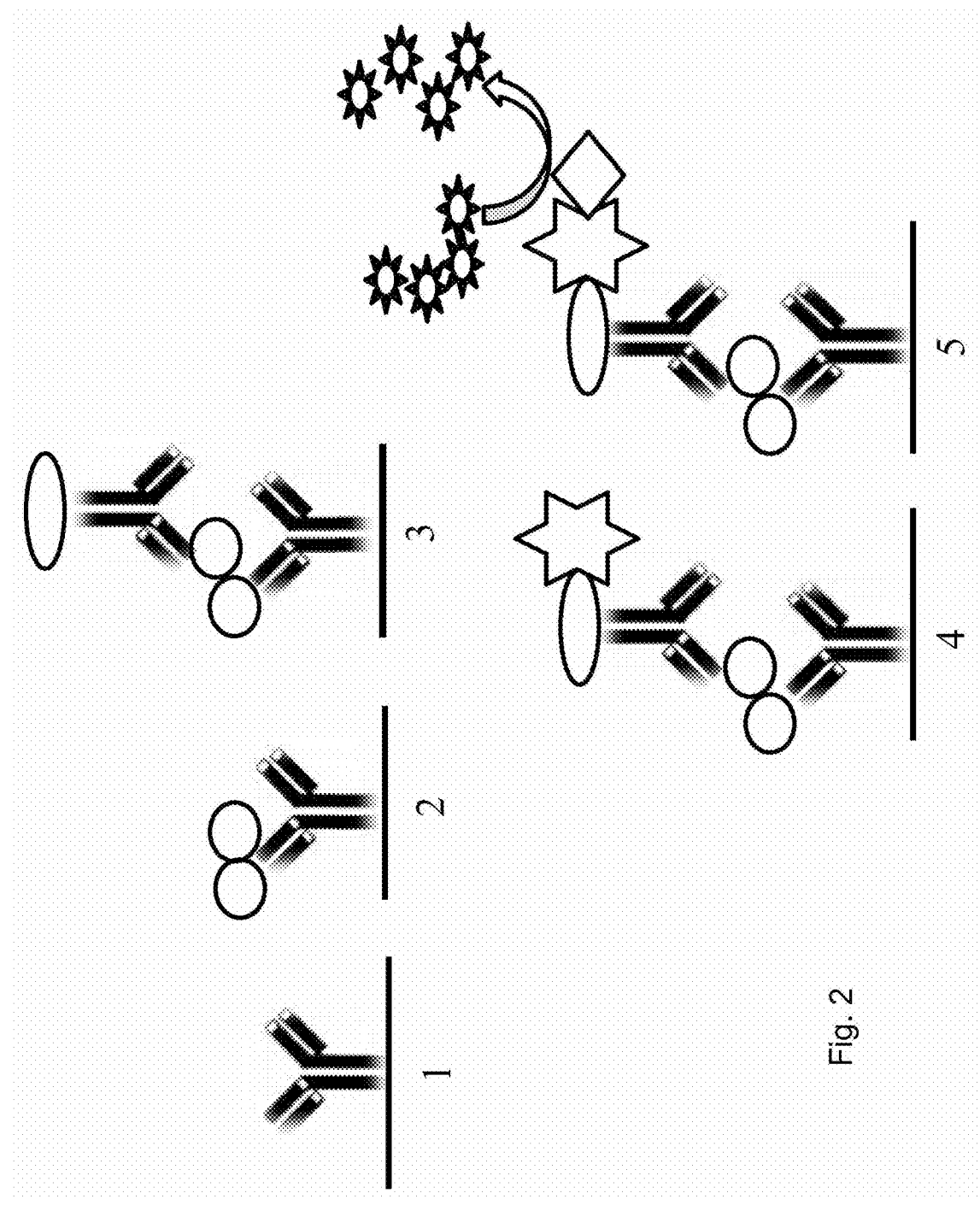
FIG. 2 is a schematic presentation of a sandwich ELISA. The five steps are: (1) coating of microplate wells with a first anti-canine TK1 monoclonal antibody (capture or coating antibody), (2) binding of canine TK1 in serum to the capture antibody, (3) attachment of a biotinylated anti-TK1 monoclonal antibody (detection antibody) to canine TK1 in serum, (4) detection of biotin by streptavidin-HRP, and (5) enzymatic activity monitored by addition of 3,3-,5,5-tetramethylbenzidine (TMB) chromogenic substrate.

In an embodiment, the kit also comprises a microtiter plate (MCP) as the support to which the first monoclonal antibody, or the fragment thereof, is immobilized or is intended to be immobilized. FIG. 2 is a schematic overview of the concept of a sandwich ELISA using the first and second monoclonal antibodies according to an embodiment.

In a preferred embodiment, the capture antibody of the sandwich ELISA is CTK1-1 (mAb1) and the detection antibody is CTK1-2 (mAb2).

In another embodiment, the capture antibody of the sandwich ELISA is CTK1-2 (mAb1) and the detection antibody is CTK1-1 (mAb2).

The kit does not necessarily have to be an ELISA kit. In another embodiment, the kit uses affinity chromatography where the first monoclonal antibody, or the fragment thereof, is bound to the stationary phase, such as to a gel matrix or beads in a column. For instance, the gel matrix or beads could be made of agarose, such as SEPHAROSE®.

In such a case, canine TK1 protein present in a sample will be entrapped in the column through binding to the immobilized first monoclonal antibodies, or the fragments thereof. Following washing, the bound canine TK1 protein can be eluted and detected using the second monoclonal antibody, or the fragment thereof. For instance, the amount of eluted canine TK1 protein can be determined using Western blotting and with the second monoclonal antibody, or the fragment thereof, for TK1 detection using direct or indirect detection methods.

The support could alternatively be magnetic beads, such as DYNABEADS® magnetic beads.

The canine TK1 protein determined according to the embodiments can be canine cellular and/or serum TK1 protein, preferably canine serum TK1 (STK1) protein or molecules.

TK1 in dogs may be present in various forms depending on the presence of certain molecules, e.g., presence or absence of adenosine triphosphate (ATP); depending on the concentration of the protein, i.e., high or low concentration; depending on the type of the protein, i.e., native or recombinant TK1; and depending on the site of the protein, i.e., in serum or cytoplasma.

Generally, cytosolic and recombinant human TK1 occurs as tetramers in the presence of ATP or at high concentration, and as dimers in the absence of ATP or at low concentration. The tetramer form of cytosolic and recombinant human TK1 has high TK1 activity whereas the dimer form has lower TK1 activity. Cytosolic TK1, also referred to as cellular TK1, is TK1 present inside cells and can be isolated from such cells.

Serum TK1 (STK1), in clear contrast, can be in the form of high molecular weight complexes, such as oligomers or comprising such oligomers, having TK1 activity and dimer and tetramer forms having very low or even lacking TK1 activity. The oligomerization seems to be related to the formation of disulfide cross linking occurring in the blood. STK1 is found in the blood of a patient and can thereby be determined in, among others, a blood sample, a plasma sample or a serum sample.

The kit of the present embodiments can be used in a method for determining the level of canine TK1 protein in a sample.

Another aspect of the embodiments relates to a method for determining a level of canine TK1 protein in a sample. The method comprises contacting the sample with a first monoclonal antibody, or a fragment thereof, and a second monoclonal antibody, or a fragment thereof, of a kit according to the embodiments. The method also comprises detecting an amount of bound second monoclonal antibody, or the fragment thereof. The level of canine TK1 protein in the sample is then determined based on the detected amount of bound second monoclonal antibody, or the fragment thereof.

Any prior art techniques to detect the amount of bound monoclonal antibody, or the fragment thereof, can be used in the present method. For instance, the detection can be direct or indicted, and may generate a fluorescent or chromogenic signal. Direct detection typically involves the use of a monoclonal antibody, or a fragment thereof, that is conjugated to a label. Indirect detection utilizes a labeled secondary antibody raised against the host species of the monoclonal antibody, or the fragment thereof.

Commonly used labels for visualization of binding of monoclonal antibody, or a fragment thereof, to epitope includes fluorophores and enzymes that convert soluble substrates into chromogenic end products.

In an embodiment, the method also comprises correlating the detected or measured amount of second monoclonal antibody, or the fragment thereof, bound to the canine TK1 protein to a level of canine TK1 protein. This may be performed using a pre-defined correlation between detected or measured amount of second monoclonal antibody, or the fragment thereof, bound to a reference TK1 protein and concentration of the reference TK1 protein. A typical reference TK1 protein that can be used when generating such a pre-defined correlation is recombinant canine TK1.

The pre-defined correlation may, thus, be generated by contacting different samples comprising different concentrations of the reference TK1 protein, preferably recombinant canine TK1, with the first monoclonal antibody, or the fragment thereof, and the second monoclonal antibody, or the fragment thereof, of the kit according to the embodiments. The amount of second monoclonal antibody, or the fragment thereof, bound to the reference TK1 protein, preferably recombinant canine TK1, is then measured in the different samples to thereby get a standard curve, function or relationship between concentration of reference TK1 protein, preferably recombinant canine TK1, and the measured amount of second monoclonal antibody, or the fragment thereof, bound to the reference TK1 protein, preferably recombinant canine TK1. This pre-defined correlation, such as standard curve, function or relationship, can then be used to map or convert the detected or measured amount of second monoclonal antibody, or the fragment thereof, bound to the canine TK1 protein in the sample to a concentration of the canine TK1 protein in the sample.

In an embodiment, the sample is processed prior to or during the incubation of the sample with the first and second monoclonal antibodies, or the fragments thereof. This sample processing may be used to stabilize selected TK1 forms in the sample and/or to break larger TK1 complexes or oligomers into smaller complexes or multimers.

Hence, in an embodiment, a sample dilution or pretreatment buffer is added to the sample prior to or in connection with contacting the sample with the first and second monoclonal antibodies, or the fragments thereof.

In an embodiment, the sample dilution buffer comprises ATP, preferably in a concentration selected within an interval of from 0.5 mM up to 50 mM, such as from 0.5 mM up to 20 mM or from 1.5 mM up to 50 mM. As previously described herein, ATP stabilizes the tetramer form of TK1, which has high enzymatic TK1 activity.

In another embodiment, the sample dilution buffer comprises a reducing agent. The reducing agent may then break disulfide cross links in larger TK1 complexes and oligomers to obtain smaller TK1 forms, such as tetramers. Various reducing agents capable of breaking disulfide bonds can be used according to the embodiments including, but not limited to, dithioerythritol (DTE), dithiothreitol (DTT), dithiobutylamin (DTBA), tris(2-carboxyethyl)phosphine) (TCEP), and combinations thereof. The amount of the reducing agent is typically selected within an interval of from 0.1 mM up to 10 mM.

The sample dilution buffer may, in an embodiment, comprise both ATP and a reducing agent. The sample is preferably a body sample and is more preferably selected from a group consisting of a cell sample, a tissue sample, a blood sample, a serum sample, a cerebrospinal fluid sample, a pleural fluid sample, a synovial fluid sample and a peritoneal cavity fluid sample. In a preferred embodiment, the body sample is a body fluid sample and preferably selected from a group consisting of a blood sample, a serum sample, a cerebrospinal fluid sample, a pleural fluid sample, a synovial fluid sample and a peritoneal cavity fluid sample. In a particular embodiment, the body (fluid) sample is a blood sample or a serum sample.

Thus, the monoclonal antibodies, or fragments thereof, of the embodiments can be used to determine a level, i.e., an amount, of canine TK1 protein in a sample. The monoclonal antibodies, or the fragments thereof, of the embodiments are believed to be able to bind to and thereby enable determination of the level of canine cellular or serum TK1 in its various forms, such as dimers, tetramers, and oligomers, including potentially bound to further proteins, co-factors or molecules. Thus, canine cellular and/or serum TK1 protein thereby includes the canine cellular and/or serum TK1 in its various forms.

In a particular embodiment, the method is a method for determining a level of canine STK1 protein in a body sample.

In another embodiment, the method is a method for determining a level of canine cellular TK1 protein in a body sample.

In a further embodiment, the method is a method for determining a level of canine cellular TK1 protein and canine STK1 protein in a body sample.

A further aspect of the embodiments relates to a method for estimating the likelihood of recurrence of a tumor disease in a canine subject, i.e., a dog. The method comprises determining a level of canine TK1 protein in a body sample from the canine subject using a method or a kit according to the embodiments. The level of canine TK1 protein in the body sample is then compared with a level of canine TK1 protein representative of a population of healthy canine subjects or with a level of canine TK1 protein previously determined in the canine subject. The method further comprises estimating the likelihood of recurrence of the tumor disease in the canine subject based on the comparison.

A determined level that is higher than a level associated with a population of healthy dogs indicates an increased likelihood of recurrence of a tumor disease in the canine subject. Similarly, a determined level that is higher than a level associated with the canine subject subsequent to previous therapy indicates an increased likelihood of recurrence of a tumor disease in the canine subject.

Yet another aspect of the embodiments relates to a method for determining cell proliferation in a canine subject. The method comprises determining a level of canine TK1 protein in a body sample from the canine subject using a method or a kit according to the embodiments. The method also comprises determining the cell proliferation based on the level of canine TK1 protein in the body sample.

In a particular embodiment, a level of normal or tumor cell proliferation is determined and compared with the determined level of canine TK1 protein to determine whether the canine subject has normal or baseline cell proliferation or an elevated cell proliferation.

The present method can be used as a tool in monitoring various therapies applied to canine subjects. For instance, the method can be used to monitor anti-proliferation or anti-tumor therapy in the canine subject. In such a case, the method can be used to verify whether a selected anti-proliferation or anti-tumor therapy has the desired effect in reducing cell proliferation in the canine subject. If the therapy does not have the desired effect, i.e., no significant decrease in cell proliferation is detected, then another or a modified anti-proliferation or anti-tumor therapy can be applied to the canine subject.

A further aspect of the embodiments relates to a method for determining a proliferation process response in a canine subject suffering from a malignant disease. The method comprises determining a level of canine TK1 protein in a body sample from the canine subject using a method or a kit according to the embodiments. The method also comprises determining the proliferation process response based on the level of canine TK1 protein in the body sample. An example of such a proliferation process response could be an immune reaction or immune reaction response.

In an embodiment, at least one other biomarker for the proliferation process response may also be used in the determination.

Yet another aspect of the embodiments relates to a method for determining a level of inflammation, infection or tumor cell proliferation in a canine subject. The method comprises determining a level of canine TK1 protein in a body sample from the canine subject using a method or a kit according to the embodiments. The method also comprises determining the level of inflammation, infection or tumor cell proliferation based on the level of canine TK1 protein in the body sample. In an embodiment, at least one other biomarker for inflammation, infector or tumor cell proliferation may also be used in the determination.

A further aspect of the embodiments relates to a method for evaluating efficiency of a treatment of a malignant disease in a canine subject. The method comprises determining a level of canine TK1 protein in a body sample from the canine subject using a method or a kit according to the embodiments prior to or in connection with start of the treatment of the malignant disease. The method also comprises determining a level of canine TK1 protein in a body sample from the canine subject using the method or kit according to the embodiments during or after the treatment of the malignant disease. The method further comprises evaluating efficiency of the treatment of the malignant disease based on a comparison of the level of canine TK1 protein determined in the body sample prior to or in connection with start of the treatment of the malignant disease and the level of canine TK1 protein determined in the body sample during or after the treatment of the malignant disease.

The method and kit of the embodiments can be used to evaluate or determine efficiency of a treatment of a malignant disease in dogs. Thus, by comparing determined canine TK1 protein levels during or after the treatment with corresponding canine TK1 protein levels previously determined before the start of the treatment or in connection with the start of the treatment it is possible to determine whether the selected treatment has any medical effect in terms of reducing the canine TK1 protein level in the dog. Hence, a reduction in canine TK1 protein level in a treated dog is determined to correlate with a treatment that has effect with regard to the malignant disease, i.e., an efficient treatment. However, if no significant reduction in canine TK1 protein level is detected in a treated dog, then the particular treatment is not efficient and does not have the desired effect with regard to the malignant disease.

The tumor is preferably a hematological tumor, such as lymphoma or leukemia, or a solid tumor, such as mammary tumor, histiocytic sarcoma, mastocytoma, melanoma, hemangiosarcoma or adenocarcinoma.

Kiran Kumar 2010 disclosed production of anti-dog TK1 antibodies produced by immunizing rabbits with a 28 amino acid long peptide corresponding to amino acids 196 to 223 in dog TK1. The anti-dog TK1 antibodies, however, showed poor performance when used in an ELISA assay and had high background. Production of polyclonal antibodies against the long (28 amino acids) peptide showed large batch-to-batch variation. This is in clear contrast to present embodiments and the experimental data presented herein. The monoclonal antibodies of the present embodiments can successfully be used in an ELISA assay with high specificity and capable of discriminating between healthy canine subject and canine subjects suffering from hematological or solid tumors.

EXAMPLES

Example 1

This Example discloses a dual monoclonal TK1 ELISA that can enhance the clinical utility of TK1 as a biomarker in veterinary medicine. These results demonstrated that TK1 protein determinations using the novel dual monoclonal TK1 ELISA has the potential to serve as a valuable biomarker for detection of a major part of the several canine malignant diseases.
Materials and Methods
Serum Samples
This study was conducted using 159 samples from diseased dogs and 118 clinically healthy dogs that were collected from two sources, the Colorado State University biobank with 80 samples from dogs with lymphoma (n=36) and carcinomas (n=44) and stored in −80° C. Eighty samples from diseased dogs (lymphoma, n=39 and carcinomas, n=41) and 118 healthy dogs were collected at University Animal Hospital, Swedish University of Agricultural Sciences, Uppsala, Sweden, and stored at −20° C. until analysis. Data covering blood count, biochemistry panel, and urinalysis were gathered for all dogs. The dogs with tumors were naive and had not received any prior antitumor treatment for cancer.

The group of healthy dogs was considered healthy based on medical history, physical examination, hematology, and a basic biochemistry analysis. These subjects were mainly recruited from the group of voluntary blood donor dogs at the University Animal Hospital.
Serum Samples and Specimen Handling
Serum samples from dogs with naive malignancies and from healthy dogs were collected over a 4-year period (2018-2022). At least 1 mL of blood was drawn from each patient and centrifuged within 1 h of collection. The serum samples were stored at −20° C. until analysis. This project was approved by the Swedish Animal Ethics Committee and samples were used only with the owners' signed consent
Canine Anti-TK1 Antibodies
The two dog anti-TK1 antibodies were raised against peptides from different regions of the TK1 sequence; one was produced against the active site of the enzyme, which is a conserved part of the protein and the other one was produced against the C-terminal regions, which shows several differences in case of canine TK1, FIG. 1.

Mouse monoclonal antibodies were produced by GenScript (Piscataway, NJ, USA) using a 24-amino acid synthetic peptide representing the amino acids 161-183 of the human TK1 sequence (mAb1: CAYTKRLGTEKEVEVIG-GADKYHS, SEQ ID NO: 5). The dog peptide sequence only shows one difference with a Ser in position 169 compared to a Thr in the human sequence. This was not regarded to lead to any difference in the reactivity of the antibodies produced toward dog or human TK1. The second peptide used was a 16-amino acid synthetic peptide (mAb2: CLVLVPGKPGEGKEATG, SEQ ID NO: 9), which is specific for dog TK1. In both cases an additional cysteine was added to N-terminal of the peptides that could be used to couple the peptides to KHL or bovine serum albumin, which were utilized in the immunization protocols as described (Jagarlamudi et al., 2015).

The recombinant dog TK1 was cloned and expressed in *Escherichia coli* and purified by Ni-Sepherose affinity chromatography as previously described (Hanan et al., 2012). Different concentrations of recombinant dog TK1 was used to prepare the calibrators.
ECL Dot Blot and Western Blot Analysis
ECL dot blot assay was carried out as described previously (He et al., 2000). In brief, 3 μl of recombinant enzyme at varying concentrations ranged from 20 to 0.6 ng was applied on nitrocellulose membrane (Thermo scientific, Germany). The membrane was blocked in non-fat dry milk 10% (Bio-Rad) for 1 h and then incubated with the hybridoma supernatants or antisera and incubated for overnight at 4° C. Then after the membrane was washed and incubated with a biotinylated second antibody conjugated with horseradish peroxidase directed against mouse (GE healthcare, UK) for 1 h at room temperature. Followed by adding ECL reagent. Finally, the signal was detected by ChemiDoc Imaging System BIO-RAD.

Western blot assay: recombinant canine TK1, human recombinant TK1 (10, 5 and 0.5 ng) and cytosolic TK1 from human (CEM+/−) containing 25 pg of proteins were diluted in a denaturing sample buffer, boiled, and loaded onto a 12% polyacrylamide gel. The gel was electrophoresed in SDS running buffer. The proteins were transferred to PVDF membranes (Millipore, USA) using semi-dry slot device, and the immunoblot was carried out as described in previous paragraph.

Immunoprecipitation with DYNABEADS®

Recombinant canine TK1 (5 ng and 2.5 ng) and 10× diluted serum samples from dogs with different malignancies were separately incubated with the hybridoma supernatants diluted 10× at the first screening phases and then with the purified monoclonal antibodies (4 pg/ml) for 1 h at 4° C. and 15 min at 23° C.). DYNABEADS® M-280 (Dynal® sheep anti-mouse IgG, Invitrogen) was prepared according to the manufacturer's product description and incubated with the antigen-antibody complexes for 1 h at 4° C. The beads and the complexes were transferred to the magnetic rack and the supernatants were collected and analyzed for TK1 activity. The results were represented as % of TK1 activity that was not bound to the beads.

Determination of $K_D$ and $K_{on}$ Rates

The kinetics of the interaction between the two monoclonal antibodies, mAb1 and mAb2 (150 kDa), and canine recombinant TK1 was measured by a Quartz Crystal Microbalance (QCM) technology. To characterize binding interactions, the monoclonal antibody was immobilized on the sensor surface and the sample containing recombinant canine TK1 was injected over the sensor surface. Binding data is displayed in real-time directly on a computer screen. The signal output is given in frequency (Hz) and is directly related to changes in mass on the sensor surface.

Dual Monoclonal Canine TK1 ELISA (Dual mAb ELISA)

All serum samples were analyzed using a previously described ELISA protocol with slight modifications (Jagarlamudi et al., 2015). Briefly, the mAb1 was immobilized on the microtiter plate. Dog sera of 60 μL were diluted 1:1 with sample dilution buffer (SDB, Alertix Veterinary Diagnostics AB) and recombinant dog TK1 with different concentrations ranging from 120 pg/ml to 2000 pg/mL serving as calibrators. Both serum samples and recombinant dog TK1 were pre-incubated for 1 h at room temperature (RT, 20-25° C.) and 100 μL of the calibrators and serum samples were added to each well of coated plate and incubated for 2 h. The plates were washed and incubated with biotin labelled mAb2 (3 pg/mL) for 1 h at RT. The plates were washed as described above and incubated with 100 μL of streptavidin-HRP for 30 min. After final wash, the wells were incubated with 100 μL of 1-Step Ultra TMB (Thermo Fisher Scientific) and the reactions were stopped by adding 100 μL of 1 M of HCl. The absorbance was measured at 450 nM (Tecan M-200+, Switzerland) and samples were run in duplicates. The lower limit of detection (LOD) was 50 pg/mL and the limit of quantification (LOQ) was 150 pg/mL. The curves were then analyzed with a 4-parameter non-linear regression. The TK1 protein levels in serum samples (pg/mL) were determined by using the standard curve. The cut-off value was set up based on 118 apparently healthy dogs as 2×SD above the mean. Intra assay variation at all non-zero calibration points CVs were 10% and between-run imprecision (CV) was <15% at concentrations down to 120 pg/mL.

[PH]-dThd Phosphotylation Assay

The TK1 activities in sera were measured by radiochemical assay using the DE-81 filter paper technique as described previously (Sharif et al., 2012). The reaction mixture contained Tris-HCl pH 7.6, 10 mM; DTT, 2 mM; MgCl₂, 5 mM; NaF, 5 mM; ATP, 5 mM; 5 μM [³H]-dThd and 10 μL serum in a final volume of 40 μL. The reaction mixture was incubated for 1 h at 37° C. Three aliquots of the reaction mixture were applied to the DE-81 filter paper discs (Whatman) and dried. The filters were then washed twice with 1 mM ammonium formate for 5 min and the products were eluted for 45 min in 0.1 M HCl and 0.2 M KCl. Finally, the radioactivity was measured by p scintillation liquid counting and the activity was expressed as pmol/min/mL. The cut-off value was set up based on 118 apparently healthy dogs as 2×SD above the mean. The detection limit (LOD) based on ten runs of samples with very low TK1 activity is 0.34 pmol/min/mL and the limit of quantification (LOQ) is 0.9 pmol/min/mL.

Statistical Analysis

The distributions of TK1 protein and activity levels in healthy and tumor groups were evaluated for normality using the D'Agostino and Pearson omnibus normality test. Serum TK1 protein and activity values showed Gaussian distribution in healthy group but not in diseased group. The Mann-Whitney U test was used to evaluate the difference between the groups. The Spearman's correlation coefficient (rs) and Pearson (r) were used to determine the correlation between different parameters. All statistical analysis was performed using Graph Pad Prism 5.0.4 (Graph Pad Software, La Jolla, CA, USA). The Receiver operating characteristic (ROC) curves were constructed to evaluate the performance of the TK1 assays. The level of statistical significance was set $P \leq 0.05$.

Results

Selection and Characterization of Anti-Dog TK1 Monoclonal Antibodies

Ten supernatants from selected hybridomas for each epitope were collected and screened with the dot blot assay. This led to selection of five hybridomas, which were sub-cloned twice and the final monoclonal hybridoma supernatants were screened using dot blot analyses and immuno-precipitation with DYNABEADS®. One sub-cloned hybridoma from each epitope class was identified and their antibodies further purified and characterized using immuno-precipitation and Western blot assays.

Figures 3A, 3B, 3C, 3D:
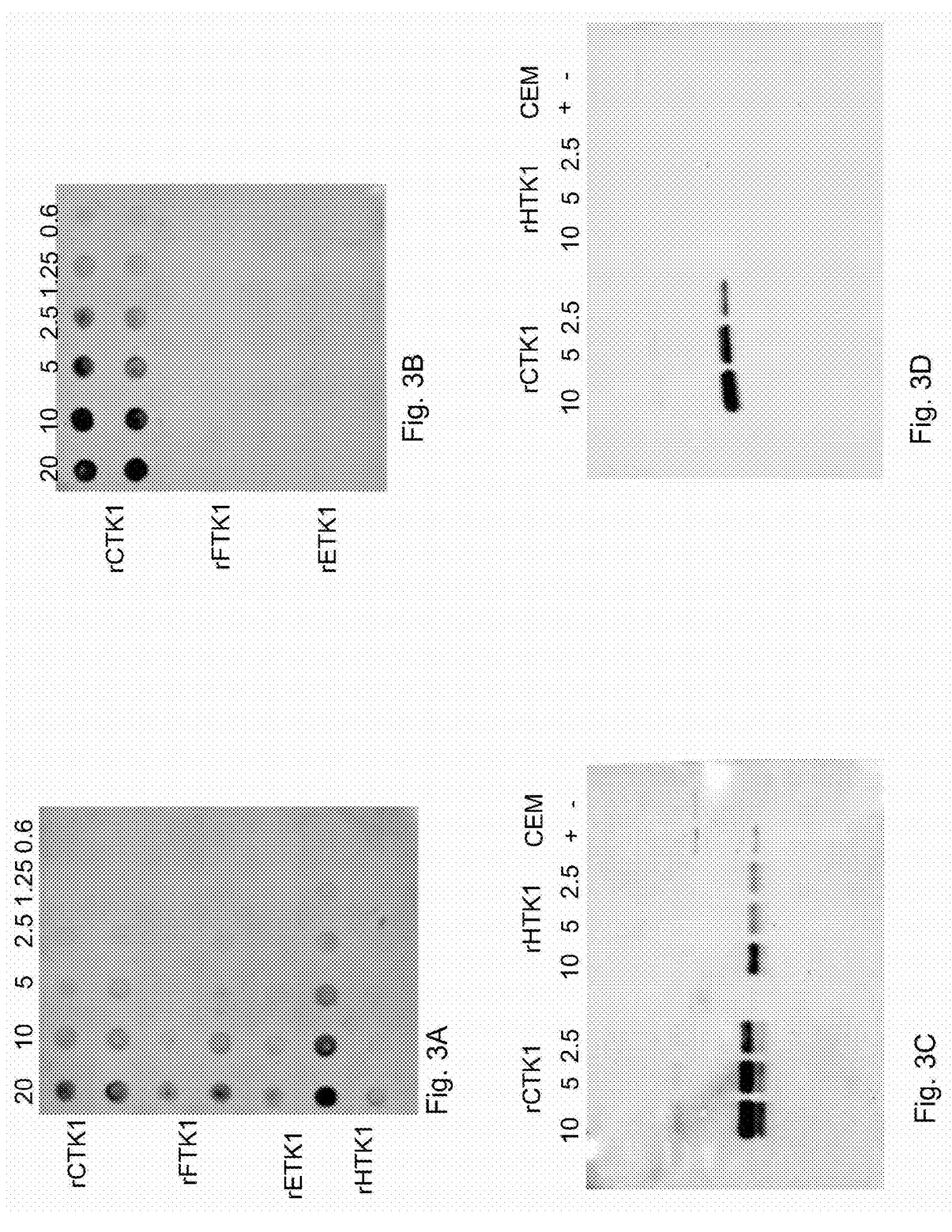
FIGS. 3A-3D show dot blot and Western blot analysis. Recombinant TK1 protein from canine (rCTK1), feline (rFTK1), equine (rETK1) and human (rHTK1) at concentration ranging from 20-0.6 ng was blotted. The membranes were developed with (FIG. 3A) monoclonal antibody produced against active site mAb1 (3 pg/mL, diluted in TBS containing 3% of non-fat dry milk) and (FIG. 3B) monoclonal antibody produced against C terminal region mAb2 (3 pg/mL, diluted in TBS containing 3% of non-fat dry milk). Recombinant dog TK1, human TK1 at concentration (10, 5 and 2.5 ng) and human TK1 positive cell extract containing 25 μg of protein (CEM TK1+) and TK1 negative cell extract containing 25 pg of protein (CEM TK1−) were electrophoresed using SDS-PAGE, followed by Western blots with 2 pg/mL of mAb1 diluted in TBS containing 3% of non-fat dry milk (FIG. 3C). Western blot results with 2 pg/mL of mAb2 diluted in TBS containing 3% of non-fat dry milk mAb 2 (FIG. 3D).

In the first dot blot, screening tests for the hybridomas supernatants was performed with recombinant TK1 proteins from canine, feline, equine, and human sources, respectively, of varying concentrations. The supernatants from hybridomas produced against the active site epitope reacted with all recombinant TK1s as seen in FIG. 3A. The result showed that supernatants against the C-terminal epitope was specific for canine TK1, since it did not react with other recombinant enzymes as shown in FIG. 3B.

SDS-PAGE with denatured recombinant TK1 (canine and human) and human cell extracts showed a strong single band stained with mAb1 (2 pg/ml, diluted in TBS containing 3% of blocking buffer) with both canine and human recombinants TK1 and wild-type of CEM cell extract (FIG. 3C). However, the membrane stained with mAb2 (2 pg/ml, diluted in TBS containing 3% blocking buffer) showed bands corresponding to ~28 kDa of recombinant canine TK1 at varying concentrations, but no bands were seen with human TK1 in agreement with the dot blot assay (FIG. 3D).

Then, the sub-clone supernatants from the selected hybridomas (five for each epitope) were analyzed again with the dot blot and the immunoprecipitation assays using magnetic beads and the dot blot results were similar to those of the first screening (data not shown). Therefore, we concluded that the selected hybridomas were monoclonal.

The immunoprecipitation (IP) results are represented as the fraction of TK1 activity that was not bound to the beads. Based on the results we have selected two positive sub-clones 9C8 (active site of TK1) and 3H11 (C-terminal of TK1) to produce mAb1 and mAb2.

The IP result with mAb1 showed that less than 5% of recombinant canine TK1 was not bound to the beads at varying concentrations and conditions (FIG. 4A). Moreover, this monoclonal antibody showed high reactivity to the serum form of TK in comparison to mAb2, where about 15-30% of serum TK1 was not bound to the beads (FIG. 4B). The IP results with mAb2 showed that 10% of recombinant canine TK1 was not bound to the beads at 4° C. and 23° C. (FIG. 4B), while 40-60% of TK1 was not bond to the beads when serum samples from dogs with leukemia, lymphoma and histiocytic sarcoma were analyzed, as seen in FIG. 4B.

Kinetic Characterization of Monoclonal Antibodies

The affinity of the monoclonal antibodies ($K_D$) was determined, the $K_D$ is the equilibrium dissociation constant. The lower $K_D$ the higher affinity of the antibody. For both monoclonal antibodies the $K_D$ was in nanomolar range. Table 1 shows the kinetic analysis of monoclonal antibodies.

TABLE 1

| Kinetic analysis of monoclonal antibodies | | | | |
|---|---|---|---|---|
| Monoclonal antibody | $K_a$ ($M^{-1}S^{-1}$) | $K_d$ ($S^{-1}$) | $K_D$ (nM) | $B_{max}$ |
| mAb1 | $2.4\text{-}3.0 \times 10^5$ | $6.1 \times 10^{-5}\text{-}2.3 \times 10^{-4}$ | 0.3-0.75 | 34-50 |
| mAb2 | $5.0\text{-}5.4 \times 10^5$ | $1.1\text{-}1.9 \times 10^{-4}$ | 0.2-0.4 | 12-10 |

Study Population

The age of the dogs in the lymphoma group (n=75) were 2-15 years old, with a median age of 8.5 years, comprised 11 males, 12 females, 29 neutered males, and 15 spayed females. While the age of 84 dogs with different carcinomas (Hemangiosarcoma 18, Histiocytic sarcoma 28, malignant mammary tumors 18, and other carcinoma e.g., melanoma, squamous cell carcinoma, renal carcinoma, liver and spleen carcinoma) were ranged from 4-16 years with a median of 9 years, comprised 6 males, 14 females, 27 neutered males and 26 neutered females. The age of dogs in the healthy control group (n=118) were 1-9 years old with a median age of 3 years, comprised 55 males, 30 females, 19 neutered males, and 2 spayed females (12 are missing). The dogs in the hematological malignancy and solid tumors groups were older than the healthy subjects (P 0.0001)

TK1 Protein and TK1 Activity Levels in Healthy Dogs and Dogs with Malignancies Determined with the Dual Monoclonal TK1 ELISA Healthy dogs: The concentration of STK1 protein was determined using the calibrator curve in the 118 healthy subjects. The TK protein was normally distributed, ranged from 11 to 331 pg/mL (median=130 pg/mL). The range of STK1 activities among the healthy subjects were from 0.39 to 2.7 pmol/min/mL (median=1.28 pmol/min/mL). The STK1 activity in healthy group was also normally distributed. In order to determine the effect of the age on the level of STK1, the healthy group was divided into two groups (above and below the median age i.e., 5 years). No significant difference was observed regarding both the TK1 activity and TK1 concentration (data not shown).

Figures 5A, 5B, 5C, 5D:
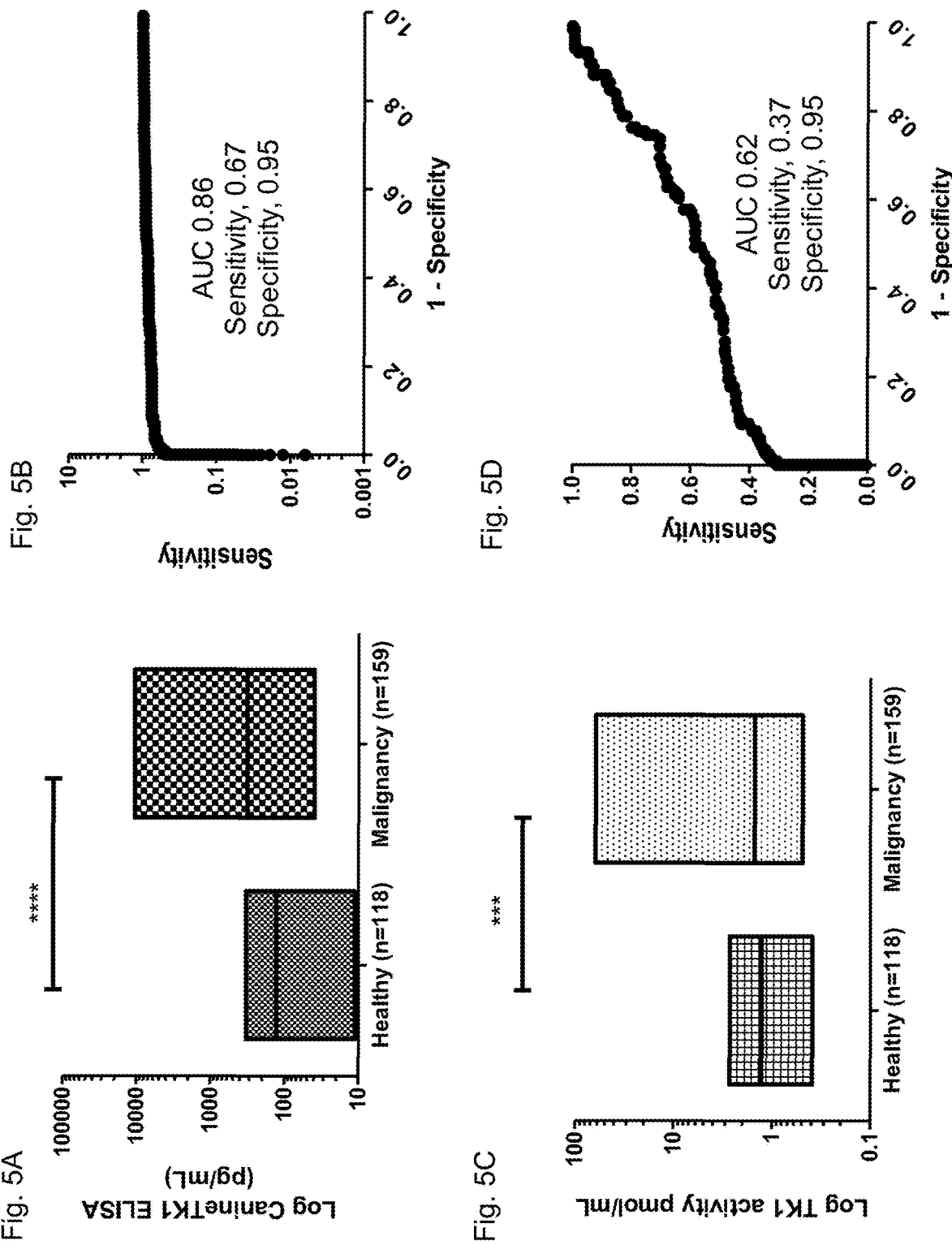
FIGS. 5A-5D show dual monoclonal TK1 ELISA in malignancy group.

Malignancy group: The concentration of STK1 were in the range of 40-10624 pg/mL, the median was 320 pg/mL, with man-Whitney test the difference was significant, P value≤0.0001 (FIG. 5A). Further analysis with ROC curve to determine the diagnostic power of the canine TK1 ELISA revealed an AUC 0.86, P<0.0001 (95% confidence interval (CI) 0.82-0.90) with sensitivity about 0.70 at 0.95 specificity (FIG. 5B). The STK1 activity values for malignancy group was ranged from 0.49 to 62 pmol/min/ml (median was 1.5 pmol/min/ml).

The activity measurement showed a significant difference between the healthy group and malignancies P value≤0.0001 (FIG. 5C). However, the ROC curve showed lower diagnostic power compared to the canine TK1 ELISA with an AUC 0.62 P<0.0001 (95% confidence interval (CI) 0.56-0.68), at 0.95 specificity, the sensitivity was about 0.40 (FIG. 5D).

Malignancy Subgroup

Lymphoma group: STK1 concentrations in the lymphoma group were in the range from 40 to 10624 pg/mL (median was 545 pg/mL). There was a significant difference between STK1 concentrations in the healthy dogs and dogs with hematologic malignancies (P≤0.0001, FIG. 6A). A ROC curve analysis was performed to evaluate the capacity of the dual mAb TK1 ELISA to differentiate dogs with lymphoma from healthy dogs. The results showed that the dual mAb TK1 ELISA assay gave an area under the curve (AUC) of 0.90, P<0.0001 (95% confidence interval (CI) 0.84-0.9), the sensitivity was 0.80 at 0.95 specificity (FIG. 6B).

Similarly, the STK1 activity values in dogs with lymphoma were 0.50 to 62 pmol/min/mL (median was 3.3 pmol/min/mL). The levels of STK1 activities were significantly higher in the lymphoma group in comparison to the healthy subjects (P≤0.0001, FIG. 6C). In ROC curve analysis, the TK1 activity assay showed an AUC of 0.81 (P<0.0001, 95% CI 0.73-0.8), and with 0.95 specificity the sensitivity was 0.61 (FIG. 6C).

Figures 7A, 7B:
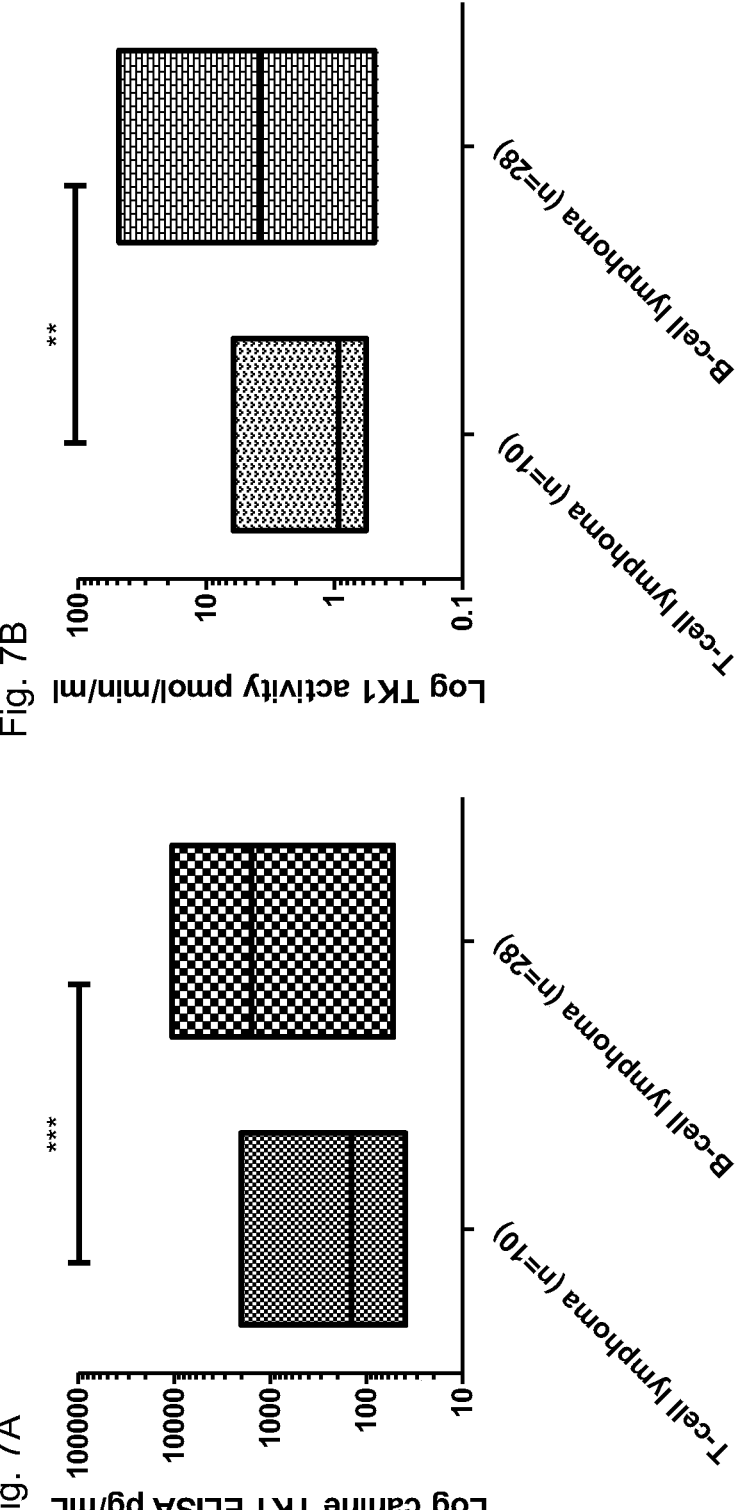
FIGS. 7A and 7B show T- and B-cell lymphoma STK1 levels. STK1 protein concentration (FIG. 7A) and STK activity values (FIG. 7B) in T-cell lymphoma (n=10) in comparison to B-cell lymphoma (n=28).

In a preliminary analysis of the STK1 protein levels in B-cell and T-cell lymphoma both TK1 ELISA (FIG. 7A) and STK1 activity levels (FIG. 7B) were significantly higher in the B-cell lymphoma group (n=28) than in the T-cell lymphoma group (n=10), P=0.0005 and P<0.002, respectively.

Other carcinomas: This group consisted of serum samples from dogs with Hemangiosarcoma (18), Histiocytic sarcoma (28), malignant mammary tumors (18), and other carcinoma e.g., melanoma, squamous cell carcinoma, renal carcinoma, liver and spleen carcinoma (3-6 of each). The STK1 concentration in this mixed carcinoma group were in the range from 70 to 4570 pg/mL (median=243 pg/mL), which was significantly higher compared to the healthy group (P 0.0001, FIG. 8A). A ROC curve analysis results showed an area under the curve (AUC) of 0.83, P<0.0001 (95% confidence interval (CI) 0.77-0.89), the sensitivity was about 0.60 at 0.95 specificity (FIG. 8B). In contrast, the activity assay could not discriminate between the healthy and carcinomas group using both Mann-Whitney test (P=0.13) or ROC curve analysis which showed an AUC of 0.54 (FIGS. 7C-7D). The STK1 activity values ranged from 0.60 to 30.5 pmol/min/mL (median 1.2 pmol/min/mL) and showed no significant differences compared to the healthy group.

The dual monoclonal TK1 ELISA showed significantly higher sensitivity than the TK1 activity assay in differentiating the group of dogs with carcinomas (0.70 vs 0.40 respectively) compared with the clinically healthy dogs. These results demonstrate that TK1 protein determinations using the dual monoclonal ELISA has the potential to serve as a valuable biomarker for detection of a major part of the canine malignant diseases.

The concept of dual monoclonal ELISA with antibodies that recognize the different sites of same antigen can increase the sensitivity of assay along with high specificity. Furthermore, use of dual mAb ELISA not only increases the shelf-life of assay but is also applicable to commercial automated assay platforms. Moreover, the detector antibody in the dual mAb ELISA is dog specific that can significantly reduce the cross-reactivity of ELISA with other species TK1. This study confirmed that the detection methods based on dual monoclonal is sensitive and easily implemented as a tool for TK1 protein determinations. The monoclonal antibody based TK1 ELISA could be of importance for estimation of cell proliferation, prognosis and therapy monitoring in veterinary oncology.

Comparison with the DiviTum TK1 and AroCell TK 210 ELISA Assays

Figure 9A:
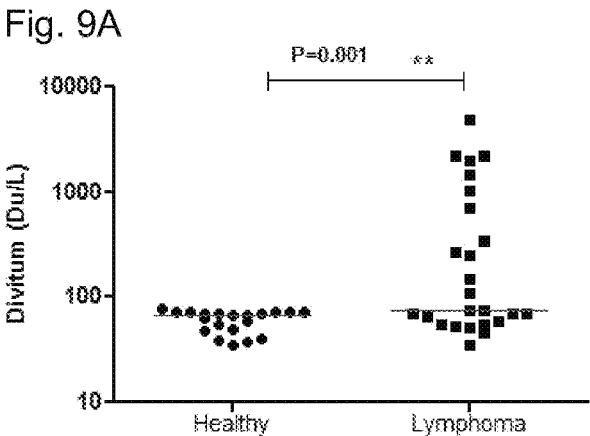
FIGS. 9A-9F show comparison of the results obtained with different TK1 assays. Mann-Whitney U test results for a subset of sera from healthy dogs (n=20) and dogs with lymphoma (n=25) measured by three different assays (FIG. 9A) DiviTum (FIG. 9B) Thd phosphorylation assay and (FIG. 9C) dual monoclonal ELISA receiver operating characteristic (ROC) curves of the STK1 distribution using (FIG. 9D) the DiviTum assay, (FIG. 9E) the Thd phosphorylation assay and (FIG. 9F) the dual monoclonal ELISA.
Figure 9B:
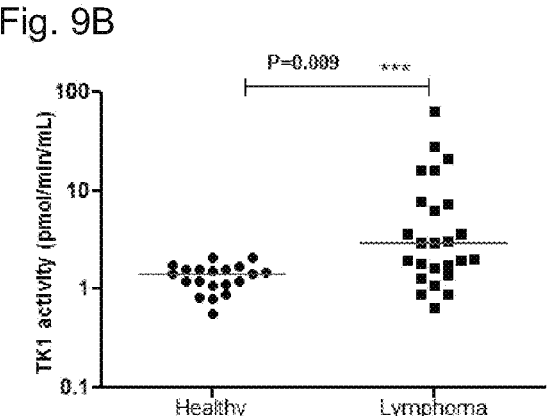
Figure 9C:
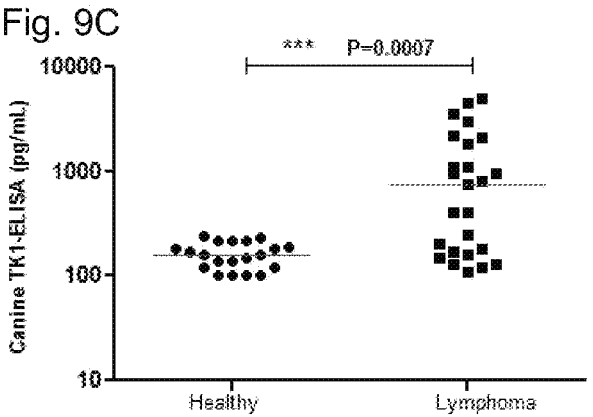
Figure 9D:
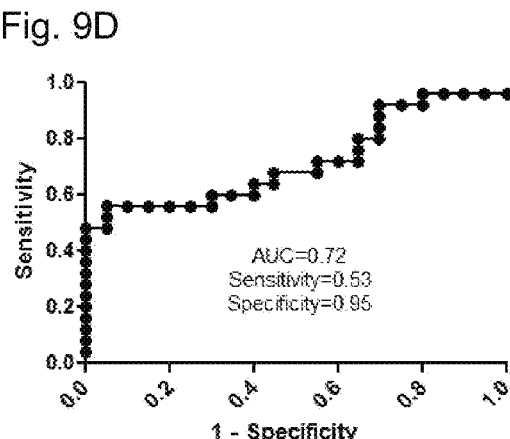
Figure 9E:
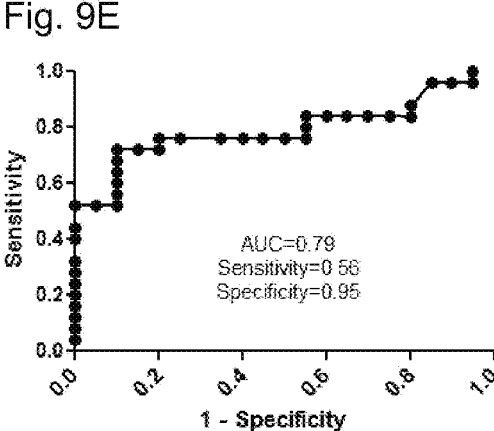
Figure 9F:
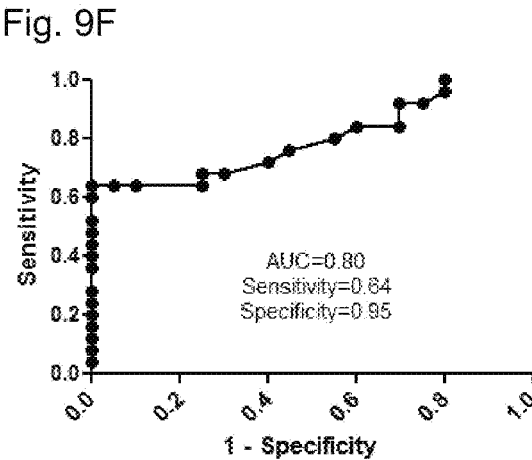

A subset of serum samples from dogs with lymphoma (n=25) and healthy dogs (n=20) were evaluated with four different TK1 assays, two of which were based on TK1 activity measurements (DiviTum assay and dThd phosphorylation assay) and two immunoassays (dual monoclonal ELISA and AroCell TK 210 ELISA). Both the TK1 activity determined with DiviTum assay as well as dThd phosphorylation assay had significantly higher levels compared to healthy and similar results were observed with dual monoclonal ELISA also (FIGS. 9A-9C). However, the ROC curve analysis demonstrates that dual monoclonal ELISA had higher sensitivity compared to the two activity assays in differentiating lymphoma from the healthy dog subgroups (FIGS. 9D-9F). The AroCell TK 210 ELISA could not detect any TK1 protein in extracts from the lymphoma or the healthy dogs.

Figure 10A:
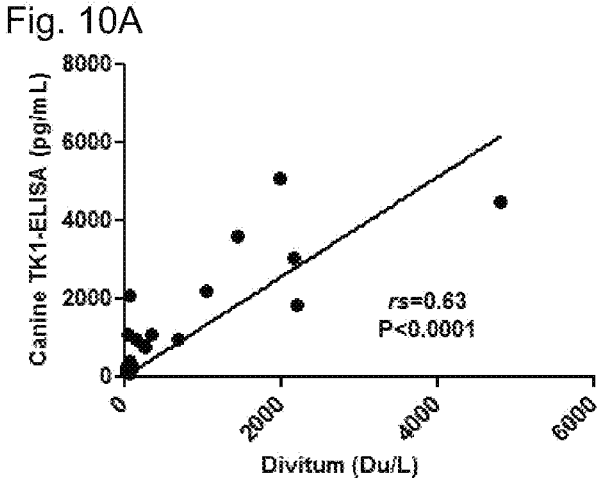
FIGS. 10A-10C show the correlations between results obtained with the different TK1 assays file. The correlation between the results obtained with a subset of sera from healthy dogs (n=20) and dogs with lymphoma (n=25) with (FIG. 10A) dual monoclonal ELISA versus the DiviTum assay, (FIG. 10B) dual monoclonal ELISA versus the dThd phosphorylation assay (FIG. 10C) the DiviTum assay versus the dThd phosphorylation assay.
Figure 10B:
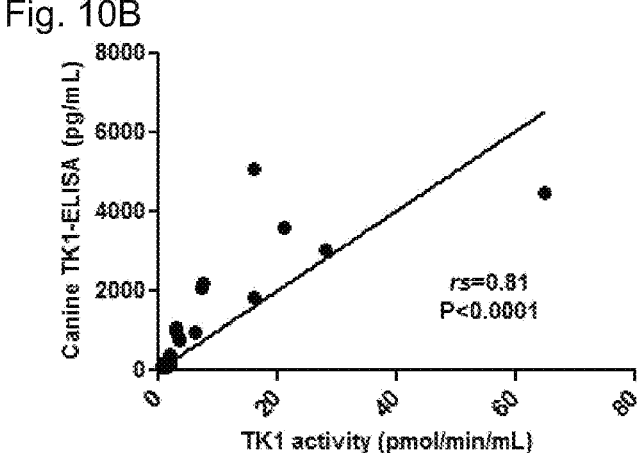
Figure 10C:
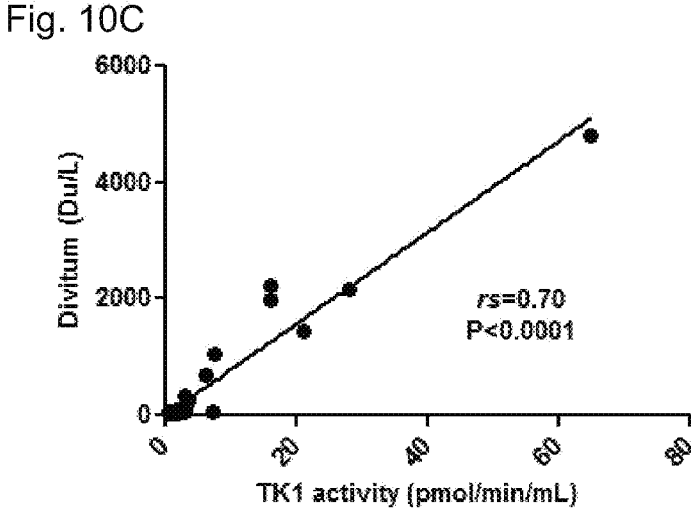

Furthermore, significant correlations were observed between the dual monoclonal ELISA and the DiviTum assay results (rs=0.63, p<0.0001; FIG. 10), and between the dual monoclonal ELISA and the dThd phosphorylation assay results (rs=0.81, p=0.0001; FIG. 10B). This was also observed with the dThd phosphorylation assay and the DiviTum assay (rs=0.7, p<0.0001; FIG. 10C) when assaying the lymphoma subgroups (N=25).

This is the first report of a dual monoclonal TK1 ELISA with sera from healthy dogs and dogs with lymphoma. Earlier studies with a poly/monoclonal antibody-based dog TK1 ELISA demonstrated similar sensitivity as the activity assay for prognosing and therapy monitoring of hematological malignancies (Jagarlamudi et al., 2015). However, there were problems with the reactivity of polyclonal antibodies such as batch-to batch variation and stability. To avoid these problems, a monoclonal ELISA would improve the production and clinical applicability of a TK1 assay in routine diagnostics. In the present Example we described the development and initial clinical evaluation of monoclonal antibody-based sandwich canine TK1 ELISA. This assay used antibodies that recognize different epitopes on the TK1 protein, which increase its sensitivity as well as specificity. Furthermore, it allows adaption to clinically used automated platforms. The antibody characterization showed that antibodies raised against the C-terminal of TK1 led to canine specificity with no cross reactivity with TK1 from other species.

Serum TK1 is a biomarker that reflects accelerated cell proliferation and cell lysis both in normal and tumor cells. The STK1 activity levels have been found to be up regulated in dogs with different malignancies but are often very low or undetectable in healthy dogs. In the present Example, about 20% of healthy dogs showed TK1 protein concentration lower than the detection limit.

This Example showed that the dual monoclonal ELISA was able to differentiate between the T-cell and B-cell lymphoma groups and this fact is of large clinical importance for the treatment and prognosis of dogs with malignant lymphoma. As expected, the results obtained with the dual monoclonal ELISA had significant correlation with other activity-based assays. Comparisons with the DiviTum assay and the classical dThd phosphorylation assay showed that these assays had overall similar sensitivity in dogs with lymphomas. However, the dual monoclonal ELISA had higher sensitivity compared to the activity-based assays.

The results presented here demonstrate that the monoclonal canine TK1 ELISA may serve as an efficient tool to estimate the aggressiveness and type of canine lymphoma assisting cancer management in veterinary medicine.

Example 2

Total RNA was isolated from the hybridoma cells 9C8 and 3H11 from Example 1 following the technical manual of TRIzol® Reagent (Ambion). Total RNA was then reverse-transcribed into cDNA using either isotype-specific anti-sense primers or universal primers following the technical manual of PrimeScript™ 1st Strand cDNA Synthesis Kit (Takara). Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided.

The isotypes of the monoclonal antibodies were mouse IgG1-κ for CTK1-1 (mAb1) and IgG2b-κ for CTK1-2 (mAb2) as determined based on an analysis of the sequences of the constant region.

```
CTK1-1 (mAb1) Heavy chain: DNA sequence
Signal sequence-FR1-CDR1-FR2-CDR2-FR3-CDR3-FR4-Constant region-Stop codon
                                                          (SEQ ID NO: 19)
ATGAAGTTGTGGCTGAACTGGATTTTCCTTGGAACACTTTTAAATGGTATCCAGTGTGAGGTGA

AGCTGGTGGAGTCTGGAGGAGGCTTGGTGCAGCCTGGGGATTCTCTGAGACTCTCCTGTGCAAC

TTCTGGGTTCACCTTCAATGATCACTACATGAACTGGGTCCGCCAGCCTCCAGGAAAGGCACTT

GAGTGGGTGGCTTTTATTGGAAACAAAGCTTATGGTTACAAAATAGAATACAATTCATCTGTGA

AGGGTCGGTTCACCATCTCCAGAGATGACTCCCAGAGCTTCCTCTATCTTCAATTGAACACCCT

GAGATCTGAGGACAGTGCCACTTATTACTGTGCAAGAGATGGTGCCTTTATTTATTGGGGCCAA

GGGACTGTGGTCACTGTCTCTGCAGCCAAAACGACACCCCCATCTGTCTATCCACTGGCCCCTG

GATCTGCTGCCCAAACTAACTCCATGGTGACCCTGGGATGCCTGGTCAAGGGCTATTTCCCTGA

GCCAGTGACAGTGACCTGGAACTCTGGATCCCTGTCCAGCGGTGTGCACACCTTCCCAGCTGTC
```

-continued

CTGCAGTCTGACCTCTACACTCTGAGCAGCTCAGTGACTGTCCCCTCCAGCACCTGGCCCAGCG

AGACCGTCACCTGCAACGTTGCCCACCCGGCCAGCAGCACCAAGGTGGACAAGAAAATTGTGCC

CAGGGATTGTGGTTGTAAGCCTTGCATATGTACAGTCCCAGAAGTATCATCTGTCTTCATCTTC

CCCCCAAAGCCCAAGGATGTGCTCACCATTACTCTGACTCCTAAGGTCACGTGTGTTGTGGTAG

ACATCAGCAAGGATGATCCCGAGGTCCAGTTCAGCTGGTTTGTAGATGATGTGGAGGTGCACAC

AGCTCAGACGCAACCCCGGGAGGAGCAGTTCAACAGCACTTTCCGCTCAGTCAGTGAACTTCCC

ATCATGCACCAGGACTGGCTCAATGGCAAGGAGTTCAAATGCAGGGTCAACAGTGCAGCTTTCC

CTGCCCCCATCGAGAAAACCATCTCCAAAACCAAAGGCAGACCGAAGGCTCCACAGGTGTACAC

CATTCCACCTCCCAAGGAGCAGATGGCCAAGGATAAAGTCAGTCTGACCTGCATGATAACAGAC

TTCTTCCCTGAAGACATTACTGTGGAGTGGCAGTGGAATGGGCAGCCAGCGGAGAACTACAAGA

ACACTCAGCCCATCATGGACACAGATGGCTCTTACTTCGTCTACAGCAAGCTCAATGTGCAGAA

GAGCAACTGGGAGGCAGGAAATACTTTCACCTGCTCTGTGTTACATGAGGGCCTGCACAACCAC

CATACTGAGAAGAGCCTCTCCCACTCTCCTGGTAAATGA

CTK1-1 (mAb1) Heavy chain: Amino acid sequence
Signal peptide-FR1-CDR1-FR2-CDR2-FR3-CDR3-FR4-Constant region
                                                              (SEQ ID NO: 20)
MKLWLNWIFLGTLLNGIQCEVKLVESGGGLVQPGDSLRLSCATSGFTENDHYMNWVRQPPGKAL

EWVAFIGNKAYGYKIEYNSSVKGRFTISRDDSQSFLYLQLNTLRSEDSATYYCARDGAFIYWGQ

GTVVTVSAAKTTPPSVYPLAPGSAAQTNSMVTLGCLVKGYFPEPVTVTWNSGSLSSGVHTEPAV

LQSDLYTLSSSVTVPSSTWPSETVTCNVAHPASSTKVDKKIVPRDCGCKPCICTVPEVSSVFIF

PPKPKDVLTITLTPKVTCVVVDISKDDPEVQFSWFVDDVEVHTAQTQPREEQFNSTFRSVSELP

IMHQDWLNGKEFKCRVNSAAFPAPIEKTISKTKGRPKAPQVYTIPPPKEQMAKDKVSLTCMITD

FFPEDITVEWQWNGQPAENYKNTQPIMDTDGSYFVYSKLNVQKSNWEAGNTFTCSVLHEGLHNH

HTEKSLSHSPGK

CTK1-1 (mAb1) Light chain: DNA sequence
Signal sequence-FR1-CDR1-FR2-CDR2-FR3-CDR3-FR4-Constant region-Stop codon
                                                              (SEQ ID NO: 21)
ATGAAGTTGCCTGTTAGGCTGTTGGTGCTGATGTTCTGGATTCCTGCTTCCAGCAGTGATGTTG

TGATGACCCAAACTCCACTCTCCCTGCCTGTCAGTCTTGGAGATCAAGCCTCCATCTCTTGCAG

ATCTAGTCAGAGCCTTGTACACAGTAATGGAAACACCTATTTACATTGGTACCTGCAGAAGCCA

GGCCAGTCTCCAAAGCTCCTGATCTACAAAGTTTCCAACCGATTTTCTGGGGTCCCAGACAGGT

TCAGTGGCAGTGGATCAGGGTCAGATTTCACACTCAAGATCAGCAGAGTGGAGGCTGAGGATCT

GGGAGTTTATTTCTGCTCTCAAAGTACACATATTCCGTACACGTTCGGAGGGGGGACCGAGCTG

GAGATAAGACGGGCTGATGCTGCACCAACTGTATCCATCTTCCCACCATCCAGTGAGCAGTTAA

CATCTGGAGGTGCCTCAGTCGTGTGCTTCTTGAACAACTTCTACCCCAAAGACATCAATGTCAA

GTGGAAGATTGATGGCAGTGAACGACAAAATGGCGTCCTGAACAGTTGGACTGATCAGGACAGC

AAAGACAGCACCTACAGCATGAGCAGCACCCTCACGTTGACCAAGGACGAGTATGAACGACATA

ACAGCTATACCTGTGAGGCCACTCACAAGACATCAACTTCACCCATTGTCAAGAGCTTCAACAG

GAATGAGTGTTAG

CTK1-1 (mAb1) Light chain: Amino acid sequence
Signal peptide-FR1-CDR1-FR2-CDR2-FR3-CDR3-FR4-Constant region
                                                              (SEQ ID NO: 22)
MKLPVRLLVLMFWIPASSSDVVMTQTPLSLPVSLGDQASISCRSSQSLVHSNGNTYLHWYLQKP

GQSPKLLIYKVSNRFSGVPDRESGSGSGSDFTLKISRVEAEDLGVYFCSQSTHIPYTFGGGTEL

-continued

EIRRADAAPTVSIFPPSSEQLTSGGASVVCFLNNFYPKDINVKWKIDGSERQNGVLNSWTDQDS

KDSTYSMSSTLTLTKDEYERHNSYTCEATHKTSTSPIVKSENRNEC

CTK1-2 (mAb2) Heavy chain: DNA sequence
Signal sequence-FR1-CDR1-FR2-CDR2-FR3-CDR3-FR4-Constant region-Stop codon
                                             (SEQ ID NO: 23)
ATGAAATGCAGCTGGGTTATCTTCTTCCTGATGGCAGTGGTAACAGGGGTCAATTCAGAGGTTC

AACTACAGCAGTCTGGGGCAGAGCTTGTGAAGCCAGGGGCCTCAGTCAAATTGTCCTGCACAGC

TTCTGGCTTCAACATTAAAGACACCTATATGCACTGGGTGAAACAGAGGCCTGAACAGGGCCTG

GAGTGGATTGGAAGGATTGATCCTGCGAATGGTAATACTAAATATGACCCGAAGTTCCAGGGCA

AGGCCACTATAACACCAGACACATCCTCCACCACAGCCTACCTGCAGCTCAGCAGCCTGACATC

TGAGGACACTGCCGTCTATTACTGTGCTAGA**AATCGGGCCTACTATGGTAACTACTATGCTATG

GACTAC**TGGGGTCAAGGAACCTCAGTCACCGTCTCCTCAGCCAAAACAACACCCCCATCAGTCT

ATCCACTGGCCCCTGGGTGTGGAGATACAACTGGTTCCTCCGTGACTCTGGGATGCCTGGTCAA

GGGCTACTTCCCTGAGTCAGTGACTGTGACTTGGAACTCTGGATCCCTGTCCAGCAGTGTGCAC

ACCTTCCCAGCTCTCCTGCAGTCTGGACTCTACACTATGAGCAGCTCAGTGACTGTCCCCTCCA

GCACCTGGCCAAGTCAGACCGTCACCTGCAGCGTTGCTCACCCAGCCAGCAGCACCACGGTGGA

CAAAAAACTTGAGCCCAGCGGGCCCATTTCAACAATCAACCCCTGTCCTCCATGCAAGGAGTGT

CACAAATGCCCAGCTCCTAACCTCGAGGGTGGACCATCCGTCTTCATCTTCCCTCCAAATATCA

AGGATGTACTCATGATCTCCCTGACACCCAAGGTCACGTGTGTGGTGGTGGATGTGAGCGAGGA

TGACCCAGACGTCCAGATCAGCTGGTTTGTGAACAACGTGGAAGTACACACAGCTCAGACACAA

ACCCATAGAGAGGATTACAACAGTACTATCCGGGTGGTCAGCACCCTCCCCATCCAGCACCAGG

ACTGGATGAGTGGCAAGGAGTTCAAATGCAAGGTCAACAACAAAGACCTCCCATCACCCATCGA

GAGAACCATCTCAAAAATTAAAGGGCTAGTCAGAGCTCCACAAGTATACATCTTGCCGCCACCA

GCAGAGCAGTTGTCCAGGAAAGATGTCAGTCTCACTTGCCTGGTCGTGGGCTTCAACCCTGGAG

ACATCAGTGTGGAGTGGACCAGCAATGGGCATACAGAGGAGAACTACAAGGACACCGCACCAGT

CCTGGACTCTGACGGTTCTTACTTCATATATAGCAAGCTCAATATGAAAACAAGCAAGTGGGAG

AAAACAGATTCCTTCTCATGCAACGTGAGACACGAGGGTCTGAAAAATTACTACCTGAAGAAGA

CCATCTCCCGGTCTCCGGGTAAATGA

CTK1-2 (mAb2) Heavy chain: Amino acid sequence
Signal peptide-FR1-CDR1-FR2-CDR2-FR3-CDR3-FR4-Constant region
                                             (SEQ ID NO: 24)
MKCSWVIFFLMAVVTGVNSEVQLQQSGAELVKPGASVKLSCTASGENIKDTYMHWVKQRPEQGL

EWIGRIDPANGNTKYDPKFQGKATITPDTSSTTAYLQLSSLTSEDTAVYYCAR**NRAYYGNYYAM

DY**WGQGTSVTVSSAKTTPPSVYPLAPGCGDTTGSSVTLGCLVKGYFPESVTVTWNSGSLSSSVH

TFPALLQSGLYTMSSSVTVPSSTWPSQTVTCSVAHPASSTTVDKKLEPSGPISTINPCPPCKEC

HKCPAPNLEGGPSVFIFPPNIKDVLMISLTPKVTCVVVDVSEDDPDVQISWFVNNVEVHTAQTQ

THREDYNSTIRVVSTLPIQHQDWMSGKEFKCKVNNKDLPSPIERTISKIKGLVRAPQVYILPPP

AEQLSRKDVSLTCLVVGENPGDISVEWTSNGHTEENYKDTAPVLDSDGSYFIYSKLNMKTSKWE

KTDSFSCNVRHEGLKNYYLKKTISRSPGK

CTK1-2 (mAb2) Light chain: DNA sequence
Signal sequence-FR1-CDR1-FR2-CDR2-FR3-CDR3-FR4-Constant region-Stop codon
                                             (SEQ ID NO: 25)
ATGGAATCACAGACTCAGGTCCTCATGTCCCTGCTGTTCTGGGTATCTGGTACCTGTGGGGACA

TTGTGATGACACAGTCTCCATCCTCCCTGACTGTGACAGCAGGAGAGAAGGTCACTATGAGCTG

CAAGTCCAGTCAGAGTCTATTAAACAGTCGAAATCAAAAGAACTACTTGACCTGGTACCAGCAG

-continued
AAACCAGGGCAGCCTCCTAAACTGTTGATCTACTGGGCATCCACTAGGGAATCTGGGGTCCCTG

ATCGCTTCACAGGCAGTGGATTTGGAACAGATTTCACTCTCGCCATCAGCAGTGTGCAGGCTGA

AGACCTGGCAGTTTATTATTGTCAAAATGATTATAGTTATCCATTCACGTTCGGCTCGGGGACA

AAGTTGGAAATAAAACGGGCTGATGCTGCACCAACTGTATCCATCTTCCCACCATCCAGTGAGC

AGTTAACATCTGGAGGTGCCTCAGTCGTGTGCTTCTTGAACAACTTCTACCCCAAAGACATCAA

TGTCAAGTGGAAGATTGATGGCAGTGAACGACAAAATGGCGTCCTGAACAGTTGGACTGATCAG

GACAGCAAAGACAGCACCTACAGCATGAGCAGCACCCTCACGTTGACCAAGGACGAGTATGAAC

GACATAACAGCTATACCTGTGAGGCCACTCACAAGACATCAACTTCACCCATTGTCAAGAGCTT

CAACAGGAATGAGTGTTAG

CTK1-2 (mAb2) Light chain: Amino acid sequence
Signal peptide-FR1-CDR1-FR2-CDR2-FR3-CDR3-FR4-Constant region
                                                          (SEQ ID NO: 26)
MESQTQVLMSLLFWVSGTCGDIVMTQSPSSLTVTAGEKVTMSCKSSQSLLNSRNQKNYLTWYQQ

KPGQPPKLLIYWASTRESGVPDRFTGSGFGTDFTLAISSVQAEDLAVYYCQNDYSYPFTFGSGT

KLEIKRADAAPTVSIFPPPSSEQLTSGGASVVCFLNNFYPKDINVKWKIDGSERQNGVLNSWTDQ

DSKDSTYSMSSTLTLTKDEYERHNSYTCEATHKTSTSPIVKSENRNEC

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Hanan, S., Jagarlamudi, KK., Wang, LY., Ellen, H., Eriksson, S., 2012. Quaternary structures of recombinant, cellular, and serum forms of Thymidine Kinase 1 from dogs and humans. *BMC Biochemistry*, 13: Article no. 12.

He, Q., Zou, L., Zhang, PA., Liu, JX., Skog, S., Fornander, T., 2000. The clinical significance of thymidine kinase 1 measurement in serum of breast cancer patients using anti-TK1 antibody. *International Journal of Biological Markers* 15(2): 139-146.

Jagarlamudi, KK., Westberg, S., Ronnberg, H., Eriksson, S., 2014. Properties of cellular and serum forms of thymidine kinase 1 (TK1) in dogs with acute lymphocytic leukemia (ALL) and canine mammary tumors (CMTs): implications for TK1 as a proliferation biomarker. *BMC veterinary research,* 10:228.

Jagarlamudi, KK., Moreau, L., Westberg, S., Ronnberg, H., Eriksson, S., 2015. A new sandwich ELISA for quantification of thymidine kinase 1 protein levels in sera from dogs with different malignancies can aid in disease management. *PLoS One* 10(9): e0137871.

Kiran Kumar, J., Sharif, H., Westberg, S., von Euler, H., Eriksson, S., 2013. High levels of inactive thymidine kinase 1 polypeptide in sera from dogs with solid tumours by immunoaffinity methods: Implications for in vitro diagnostics. *The Veterinary Journal* 197, 854-860.

Kiran Kumar. J., Immunoassays for detection of serum Thymidine Kinase 1 in Dog lymphomas and carcinomas, *Master Thesis in Animal Sciences, Uppsala* 2010.

Sharif, H., von Euler, H., Westberg, S., He, E., Wang, L., Eriksson, S., 2012. A sensitive and kinetically defined radiochemical assay for canine and human serum thymidine kinase (TK1) to monitor canine lymphoma. *The Veterinary Journal* 194, 40-47.

von Euler, H., Ohrvik, A. B., Eriksson, S. K., 2006. A non-radiometric method for measuring serum thymidine kinase activity in malignant lymphomas in dogs. *Research in Veterinary Science* 80, 17-24.

The invention claimed is:

1. A kit for determining a level of canine thymidine kinase 1 (TK1) protein in a sample, comprising:

two monoclonal antibodies or fragments thereof, either one of which is immobilized to a support;

wherein (a) one of the two monoclonal antibodies or the fragment thereof comprises:

a variable heavy (VH) complementary determining region 1 (CDR1) having amino acid sequence SEQ ID NO: 19, a VH CDR2 having amino acid sequence SEQ ID NO: 20, a VH CDR3 having amino acid sequence SEQ ID NO: 21, a variable light (VL) CDR1 having amino acid sequence SEQ ID NO: 22, a VL CDR2 having amino acid sequence SEQ ID NO: 23, and a VL CDR3 having amino acid sequence SEQ ID NO: 24; and (b) the other of the two monoclonal antibodies or the fragment thereof comprises a VH CDR1 having amino acid sequence SEQ ID NO: 37, a VH CDR2 having amino acid sequence SEQ ID NO: 38, a VH CDR3 having amino acid sequence SEQ ID NO: 39, a VL CDR1 having amino acid sequence SEQ ID NO: 40, a VL CDR2 having amino acid sequence SEQ ID NO: 41, and a VL CDR3 having amino acid sequence SEQ ID NO: 42.

2. The kit according to claim 1, wherein the one of the two monoclonal antibodies or the fragment thereof has specificity for a peptide consisting of an amino acid sequence selected from the group consisting of SEQ ID NO: 5 and SEQ ID NO: 6.

3. The kit according to claim 1, wherein the other of the two monoclonal antibodies or the fragment thereof has specificity for a peptide consisting of an amino acid sequence selected from the group consisting of SEQ ID NO: 9 and SEQ ID NO: 10.

4. The kit according to claim 1, wherein the one of the two monoclonal antibodies or the fragment thereof has:

a VH framework 1 (FR1) having amino acid sequence SEQ ID NO: 25;

a VH FR2 having amino acid sequence SEQ ID NO: 26;

a VH FR3 having amino acid sequence SEQ ID NO: 27;

a VH FR4 having amino acid sequence SEQ ID NO: 28;

a VL FR1 having amino acid sequence SEQ ID NO: 29;

a VL FR2 having amino acid sequence SEQ ID NO: 30;

a VL FR3 having amino acid sequence SEQ ID NO: 31; and a VL FR4 having amino acid sequence SEQ ID NO: 32.

5. The kit according to claim 4, wherein the one of the two monoclonal antibodies or the fragment thereof has a heavy chain having amino acid sequence SEQ ID NO: 35 and a light chain having amino acid sequence SEQ ID NO: 36.

6. The kit according to claim 1, wherein the other of the two monoclonal antibodies or the fragment thereof has:

a VH FR1 having amino acid sequence SEQ ID NO: 43;

a VH FR2 having amino acid sequence SEQ ID NO: 44;

a VH FR3 having amino acid sequence SEQ ID NO: 45;

a VH FR4 having amino acid sequence SEQ ID NO: 46;

a VL FR1 having amino acid sequence SEQ ID NO: 47;

a VL FR2 having amino acid sequence SEQ ID NO: 48;

a VL FR3 having amino acid sequence SEQ ID NO: 49; and a VL FR4 having amino acid sequence SEQ ID NO: 50.

7. The kit according to claim 6, wherein the other of the two monoclonal antibodies or the fragment thereof has a variable heavy chain having amino acid sequence SEQ ID NO: 51 and a varaible light chain having amino acid sequence SEQ ID NO: 52.

8. The kit according to claim 7, wherein the other of the two monoclonal antibodies or the fragment thereof has a heavy chain having amino acid sequence SEQ ID NO: 53 and a light chain having amino acid sequence SEQ ID NO: 54.

9. The kit according to claim 1, wherein the kit is a sandwich assay kit.

10. The kit according to claim 1, wherein the kit is an Enzyme-Linked Immunosorbent Assay (ELISA) kit.

11. The kit according to claim 1, wherein the second antibody has a covalently attached biotin or a covalently attached streptavidin or avidin.

12. The kit according to claim 11, further comprising:

a horseradish peroxidase (HRP) labeled streptavidin or avidin or a HRP labeled biotin; and a HRP substrate selected from a group consisting of a 3,3',5,5'-tetramethylbenzidine (TMB) substrate, a 3,3'-diaminobenzidine (DAB) substrate and a 2,2'-azino-bis (3-ethylbenzothiazoline-6-sulphonic acid (ABTS) substrate.

13. The kit according to claim 1, further comprising a microtiter plate as the support.

14. The kit according to claim 1, further comprising agarose beads or magnetic beads as the support.

15. A method for determining a level of canine thymidine kinase 1 (TK1) protein in a sample using the kit according to claim 1, comprising:

contacting the sample with the two monoclonal antibodies or the fragments thereof of the kit, wherein a first of the two monoclonal antibodies is immobilized on a substrate;

detecting a bound amount of a second of the two monoclonal antibodies or the fragment thereof; and determining the level of canine TK1 protein in the sample based on the detected amount of bound second antibody.

US 12,578,340 B2

16. The method according to claim 15, wherein the sample is body fluid sample.

17. The method according to claim 16, wherein the body fluid sample is selected from the group consisting of a blood sample, a plasma sample and a serum sample.

\* \* \* \* \*